US010155766B2

(12) United States Patent
Hagen et al.

(10) Patent No.: US 10,155,766 B2
(45) Date of Patent: Dec. 18, 2018

(54) PYRAZOLOPYRIMIDINE ANTIBACTERIAL AGENTS

(71) Applicant: BOARD OF TRUSTEES OF NORTHERN ILLINOIS UNIVERSITY, Dekalb, IL (US)

(72) Inventors: Timothy J. Hagen, Lisle, IL (US); Joy M. Blain, Dekalb, IL (US); Gashaw M. Goshu, Dekalb, IL (US); Brian E. Hartnett, Dekalb, IL (US)

(73) Assignee: Board of Trustees of Northern Illinois University, DeKalb, IL (US)

( * ) Notice: Subject to any disclaimer, the term of this patent is extended or adjusted under 35 U.S.C. 154(b) by 0 days.

(21) Appl. No.: 15/611,512

(22) Filed: Jun. 1, 2017

(65) Prior Publication Data

US 2017/0355700 A1 Dec. 14, 2017

Related U.S. Application Data

(60) Provisional application No. 62/350,034, filed on Jun. 14, 2016.

(51) Int. Cl.

| | |
|---|---|
| ***C07D 487/04*** | (2006.01) |
| ***A61K 31/519*** | (2006.01) |
| ***A61K 45/06*** | (2006.01) |

(52) U.S. Cl.

CPC .......... *C07D 487/04* (2013.01); *A61K 31/519* (2013.01); *A61K 45/06* (2013.01)

(58) Field of Classification Search

CPC ............................ A61K 31/519; C07D 487/04

USPC ........................................ 514/262.1; 544/262

See application file for complete search history.

(56) References Cited

U.S. PATENT DOCUMENTS

| | | | |
|---|---|---|---|
| 4,218,458 | A | 8/1980 | Heeres |
| 4,447,422 | A | 5/1984 | Taylor |
| 4,533,550 | A | 8/1985 | Heeres |
| 4,666,915 | A | 5/1987 | Ozeki |
| 2003/0004202 | A1 | 1/2003 | Elliott et al. |
| 2003/0176430 | A1 | 9/2003 | Take |
| 2003/0176454 | A1 | 9/2003 | Yamada |
| 2011/0020460 | A1 | 1/2011 | Mascitti |
| 2011/0045101 | A1 | 2/2011 | Selby |
| 2011/0046142 | A1 | 2/2011 | Lewis |
| 2011/0136796 | A1 | 6/2011 | Mautino |

FOREIGN PATENT DOCUMENTS

| | | |
|---|---|---|
| CA | 1218368 | 2/1987 |
| CH | 361283 | 4/1962 |
| EP | 0067610 | 12/1982 |
| EP | 0144730 | 6/1985 |
| GB | 859716 | 1/1961 |
| JP | S62-267229 | 11/1987 |
| JP | H05-262747 | 10/1993 |
| WO | WO 2009/127615 | 10/2009 |

OTHER PUBLICATIONS

Skipper, et. al., Cancer Research (1957), 17, 579-96.*
Cheng, et. al., Journal of Organic Chemistry (1956), 21, 1240-56.*
Avila, et. al., Comparative Biochemistry and Physiology, Part C: Pharmacology, Toxicology & Endocrinology (1986), 83C(2), 291-4.*
Noell, et. al., Journal of Organic Chemistry (1958), 23, 1547-50.*
Goshu, et. al., Bioorganic & Medicinal Chemistry Letters (2015), 25(24), 5699-5704.*
Aguirre et al, "Novel Antiprotoxoal Products: Imidazole and BenzimidazoleN-Oxide Derivatives and Related Compounds," *Archiv. Der Pharmazie*, 337(5): 259-270 (2004).
Badawey et al., 330 Archie der Pharmazie (Weinheim, Germany), 59-62 (1997).
CAS Abstract 4,447,422 (1983).
CAS Abstract of CH 361,283 (1961).
CAS Reg No. 908544-55-8 (2006).
CAS Registry No. 861211-28-1 (Aug. 21, 2005).
Rostom et al., 7 Scientia Pharmaceutica, 57-74 (2003).
Sorm et al, "Antitubercular activity of 2-amino-4-hydroxy-5-pyrimidinecarboxylic acid, pyrimidine analogue of p-amino-salicilic acid," *Chem. Listy. Pro Vedu a Prumysl*, 45: 422-423 (1951) (Abstract).
Stanovinik et al., 91 Advances in Heterocyclic Chemistry, 1-134 (2006).
Yurugi et al., 28 Takeda Kenkyusho Nenpo, 1-11 (1969).

* cited by examiner

*Primary Examiner* — Jeffrey H Murray
(74) *Attorney, Agent, or Firm* — Barnes & Thornburg LLP; Alice O. Martin

(57) ABSTRACT

Pyrazolopyrimidine compounds for inhibition of isoprenoid biosynthesis have a formula (I)

(I)

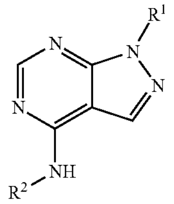

or a pharmaceutically acceptable salt thereof. In formula (I), $R^1$ includes an alkyl group and $R^2$ includes an optionally substituted moiety selected from the group consisting of an optionally substituted benzyl group, an optionally substituted phenethyl group, an optionally substituted ethanol group, an optionally substituted ethyl acetate group, an optionally substituted methyl furan group, an optionally substituted 3-ethyl indole group, and a lower alkyl group. Compositions containing pyrazolopyrimidine compounds and methods for using pyrazolopyrimidine compounds are described.

2 Claims, 5 Drawing Sheets

Specification includes a Sequence Listing.

SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gggtcctggt tcgatggtga cctcccgact cttcg 35

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
cttgttcgtg ctgtttatta actggcgcgc gccggatgc 39

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
gggtcctggt tcgatgaccg atacgacccg ctcg 34

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
cttgttcgtg ctgtttatta tgacgcgaaa gcgaagagtg ga 42

<210> SEQ ID NO 5
<211> LENGTH: 873
<212> TYPE: DNA
<213> ORGANISM: Escherichia coli

<400> SEQUENCE: 5
atggcgcatc atcatcatca tcatatgcgc acccagtggc cgagcccggc gaaactgaac 60
ctgtttctgt atattaccgg ccagcgcgcg gatggctatc ataccctgca gaccctgttt 120
cagtttctgg attatggcga taccattagc attgaactgc gcgatgatgg cgatattcgc 180
ctgctgaccc cggtggaagg cgtggaacat gaagataacc tgattgtgcg cgcggcgcgc 240
ctgctgatga aaaccgcggc ggatagcggc cgcctgccga ccggcagcgg cgcgaacatt 300
agcattgata aacgcctgcc gatgggcggc ggcctgggcg gcggcagcag caacgcggcg 360
accgtgctgg tggcgctgaa ccatctgtgg cagtgcggcc tgagcatgga tgaactggcg 420
gaaatgggcc tgaccctggg cgcggatgtg ccggtgtttg tgcgcggcca tgcggcgttt 480
gcggaaggcg tgggcgaaat tctgaccccg gtggatccgc cggaaaaatg gtatctggtg 540

-continued

```
gcgcatccgg gcgtgagcat tccgaccccg gtgattttta aagatccgga actgccgcgc    600

aacaccccga aacgcagcat tgaaaccctg ctgaaatgcg aatttagcaa cgattgcgaa    660

gtgattgcgc gcaaacgctt tcgcgaagtg gatgcggtgc tgagctggct gctggaatat    720

gcgccgagcc gcctgaccgg caccggcgcg tgcgtgtttg cggaatttga taccgaaagc    780

gaagcgcgcc aggtgctgga acaggcgccg gaatggctga acggctttgt ggcgaaaggc    840

gtgaacctga gcccgctgca tcgcgcgatg ctg                                  873
```

<210> SEQ ID NO 6
<211> LENGTH: 291
<212> TYPE: PRT
<213> ORGANISM: Escherichia coli

<400> SEQUENCE: 6

```
Met Ala His His His His His His Met Arg Thr Gln Trp Pro Ser Pro
1               5                   10                  15

Ala Lys Leu Asn Leu Phe Leu Tyr Ile Thr Gly Gln Arg Ala Asp Gly
            20                  25                  30

Tyr His Thr Leu Gln Thr Leu Phe Gln Phe Leu Asp Tyr Gly Asp Thr
        35                  40                  45

Ile Ser Ile Glu Leu Arg Asp Asp Gly Asp Ile Arg Leu Leu Thr Pro
    50                  55                  60

Val Glu Gly Val Glu His Glu Asp Asn Leu Ile Val Arg Ala Ala Arg
65                  70                  75                  80

Leu Leu Met Lys Thr Ala Ala Asp Ser Gly Arg Leu Pro Thr Gly Ser
                85                  90                  95

Gly Ala Asn Ile Ser Ile Asp Lys Arg Leu Pro Met Gly Gly Gly Leu
            100                 105                 110

Gly Gly Gly Ser Ser Asn Ala Ala Thr Val Leu Val Ala Leu Asn His
        115                 120                 125

Leu Trp Gln Cys Gly Leu Ser Met Asp Glu Leu Ala Glu Met Gly Leu
    130                 135                 140

Thr Leu Gly Ala Asp Val Pro Val Phe Val Arg Gly His Ala Ala Phe
145                 150                 155                 160

Ala Glu Gly Val Gly Glu Ile Leu Thr Pro Val Asp Pro Pro Glu Lys
                165                 170                 175

Trp Tyr Leu Val Ala His Pro Gly Val Ser Ile Pro Thr Pro Val Ile
            180                 185                 190

Phe Lys Asp Pro Glu Leu Pro Arg Asn Thr Pro Lys Arg Ser Ile Glu
        195                 200                 205

Thr Leu Leu Lys Cys Glu Phe Ser Asn Asp Cys Glu Val Ile Ala Arg
    210                 215                 220

Lys Arg Phe Arg Glu Val Asp Ala Val Leu Ser Trp Leu Leu Glu Tyr
225                 230                 235                 240

Ala Pro Ser Arg Leu Thr Gly Thr Gly Ala Cys Val Phe Ala Glu Phe
                245                 250                 255

Asp Thr Glu Ser Glu Ala Arg Gln Val Leu Glu Gln Ala Pro Glu Trp
            260                 265                 270

Leu Asn Gly Phe Val Ala Lys Gly Val Asn Leu Ser Pro Leu His Arg
        275                 280                 285

Ala Met Leu
    290
```

<210> SEQ ID NO 7
<211> LENGTH: 942
<212> TYPE: DNA
<213> ORGANISM: Burkholderia thailandensis

<400> SEQUENCE: 7

```
atggctcatc accatcacca tcatatgggt accctggaag ctcagaccca gggtcctggt     60

tcgatgaccg atacgacccg ctcgctgcgc gactgcctcg ccccggcgaa actgaacctg    120

ttcctgcaca tcacgggccg tcgtccggac ggctatcacg agctgcaaag cgtgttccag    180

ctgctcgact ggggcgaccg gctgcacttc acgctgcgcg acgacggcaa ggtgtcgcgc    240

aagaccgacg tgccgggcgt acccgaggaa accgacctca tcgtgcgcgc ggcgtcgctg    300

ctgaaagcgc acacgggcac ggcggcgggc gtcgacatcg agatcgacaa gcgactgccg    360

atgggcgcgg gcctcggcgg aggcagctcg gatgcggcga cgacgttgct cgcgctcaac    420

cgcctctgga agctcgactt gccgcgcgcc acgctgcaat cgctcgcggt gaagctcggc    480

gccgacgtgc cgttcttcgt cttcggaaaa aatgcgttcg cagagggtat cggagaagcg    540

ctgcaagctg tagaattgcc gactcgctgg tttctggttg tgacaccgcg ggttcacgtt    600

ccgaccgcag cgattttttc cgaaaaatcg ttgacaagag attcgaaacc catcacaatt    660

acggactttc ttgcacagca agactgcaac acgggatggc ctgacagttt cggtcggaat    720

gacatgcagc cggttgtgac aagcaagtac gcggaagttg caaaggtggt cggatggttt    780

tataatctga cccccgcgcg gatgaccggc tccggagcta gcgtgtttgc agcgttcaag    840

agcaaggcgg aggcaggagc ggcgcaagcc caactgccgg ccggctggga cagcgcagtt    900

gccgagagct tgggtgagca tccactcttc gctttcgcgt ca                       942
```

<210> SEQ ID NO 8
<211> LENGTH: 314
<212> TYPE: PRT
<213> ORGANISM: Burkholderia thailandensis

<400> SEQUENCE: 8

```
Met Ala His His His His His His Met Gly Thr Leu Glu Ala Gln Thr
1               5                   10                  15

Gln Gly Pro Gly Ser Met Thr Asp Thr Thr Arg Ser Leu Arg Asp Cys
            20                  25                  30

Leu Ala Pro Ala Lys Leu Asn Leu Phe Leu His Ile Thr Gly Arg Arg
        35                  40                  45

Pro Asp Gly Tyr His Glu Leu Gln Ser Val Phe Gln Leu Leu Asp Trp
    50                  55                  60

Gly Asp Arg Leu His Phe Thr Leu Arg Asp Asp Gly Lys Val Ser Arg
65                  70                  75                  80

Lys Thr Asp Val Pro Gly Val Pro Glu Glu Thr Asp Leu Ile Val Arg
                85                  90                  95

Ala Ala Ser Leu Leu Lys Ala His Thr Gly Thr Ala Ala Gly Val Asp
            100                 105                 110

Ile Glu Ile Asp Lys Arg Leu Pro Met Gly Ala Gly Leu Gly Gly Gly
        115                 120                 125

Ser Ser Asp Ala Ala Thr Thr Leu Leu Ala Leu Asn Arg Leu Trp Lys
    130                 135                 140

Leu Asp Leu Pro Arg Ala Thr Leu Gln Ser Leu Ala Val Lys Leu Gly
145                 150                 155                 160

Ala Asp Val Pro Phe Phe Val Phe Gly Lys Asn Ala Phe Ala Glu Gly
                165                 170                 175
```

-continued

```
Ile Gly Glu Ala Leu Gln Ala Val Glu Leu Pro Thr Arg Trp Phe Leu
            180                 185                 190

Val Val Thr Pro Arg Val His Val Pro Thr Ala Ala Ile Phe Ser Glu
        195                 200                 205

Lys Ser Leu Thr Arg Asp Ser Lys Pro Ile Thr Thr Thr Asp Phe Leu
    210                 215                 220

Ala Gln Gln Asp Cys Asn Thr Gly Trp Pro Asp Ser Phe Gly Arg Asn
225                 230                 235                 240

Asp Met Gln Pro Val Val Thr Ser Lys Tyr Ala Glu Val Ala Lys Val
                245                 250                 255

Val Gly Trp Phe Tyr Asn Leu Thr Pro Ala Arg Met Thr Gly Ser Gly
            260                 265                 270

Ala Ser Val Phe Ala Ala Phe Lys Ser Lys Ala Glu Ala Gly Ala Ala
        275                 280                 285

Gln Ala Gln Leu Pro Ala Gly Trp Asp Ser Ala Val Ala Glu Ser Leu
    290                 295                 300

Gly Glu His Pro Leu Phe Ala Phe Ala Ser
305                 310


<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5
```

PYRAZOLOPYRIMIDINE ANTIBACTERIAL AGENTS

CROSS REFERENCE TO RELATED APPLICATIONS

This application claims the benefit of priority under 35 U.S.C. § 119(e) to U.S. Provisional Patent Application No. 62/350,034, filed Jun. 14, 2016. The disclosure set forth in the referenced application is incorporated herein by reference in its entirety.

FEDERALLY SPONSORED RESEARCH AND DEVELOPMENT

This invention was made with government support under Grant No. R15 AI113653 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 1, 2017, is named 265034_SEQ_ST25.txt and is 9,240 bytes in size.

TECHNICAL FIELD

The present teachings relate generally to pyrazolopyrimidine compounds for the inhibition of isoprenoid biosynthesis in pathogenic organisms and, in some embodiments, to pyrazolopyrimidine compounds for use as antibacterial agents.

BACKGROUND

In the pre-antibiotic era, minor injuries and common infections could cause life-threatening illnesses. One of the greatest successes in the $20^{th}$ century was the discovery of antibiotics, which dramatically improved the quality of life and completely revolutionized modern medicine. Most of the currently used antimicrobial agents were discovered from 1945 to 1960, during the "golden era" of antibiotics. Unfortunately, the discovery of new antimicrobial drugs has significantly declined since the early 1960s. The rapid decline of new antimicrobial drugs may be related to several factors. New treatments for diseases such as hypertension and cancer are often more profitable than antibiotic drugs, leading to reduced commercial resource investment in the latter. The screening methods, chemical composition of materials and other infrastructure developed for drug discovery in other disease areas do not necessarily translate well into antibiotic research. The ability of pathogenic organisms to develop resistance mechanisms against chemotherapeutics puts an increased burden on the development of new treatments, as well as the general scientific strategy in targeting such organisms.

Although antibiotic resistance is a natural evolutionary process for bacteria adapting to their environment, it has been significantly accelerated by selective pressure employed by the overuse of antibiotics. As a result, antibacterial resistance to drugs has greatly increased worldwide and poses a global health threat. The World Health Organization warns that if appropriate measures are not taken, much of the past success in combating infectious diseases will be reversed. There is a general consensus that in order to slow down antimicrobial drug resistance, proper use of antibiotics (e.g., avoiding underuse or overuse of antibiotics), is crucial. Additionally, there is renewed interest in the discovery and development of new antimicrobial agents. There are new incentives and programs that encourage the discovery and development of new antimicrobials with the ultimate goal to bring new antibiotics more rapidly to patients in need. Investigation of new metabolic pathways that are essential for the survival of pathogenic microorganisms that could lead to the development of new antimicrobial drugs is vital.

SUMMARY

The scope of the present disclosure is defined solely by the appended claims, and is not affected to any degree by the statements within this summary.

By way of introduction, a compound in accordance with the present teachings has a formula (I)

(I)

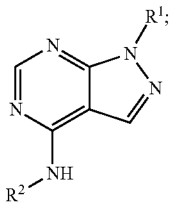

or a pharmaceutically acceptable salt thereof. In formula (I), $R^1$ includes an alkyl group and $R^2$ includes an optionally substituted moiety selected from the group consisting of an optionally substituted group of formula (II)

(II)

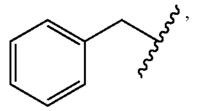

an optionally substituted group of formula (III)

(III)

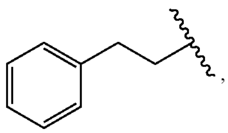

an optionally substituted group of formula (IV)

(IV)

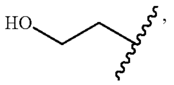

an optionally substituted group of formula (V)

(V)

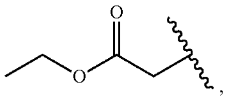

an optionally substituted group of formula (VI)

(VI)

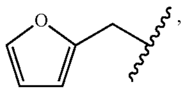

an optionally substituted group of formula (VII)

(VII)

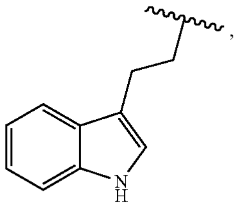

and a lower alkyl group.

Methods for the treatment of bacterial, protozoan, and/or parasitic infections in accordance with the present teachings, and methods for treating malaria and/or tuberculosis in accordance with the present teachings, include administering a therapeutically effective amount of a compound of a type described above to a patient in need thereof.

DETAILED DESCRIPTION

Figure 1:
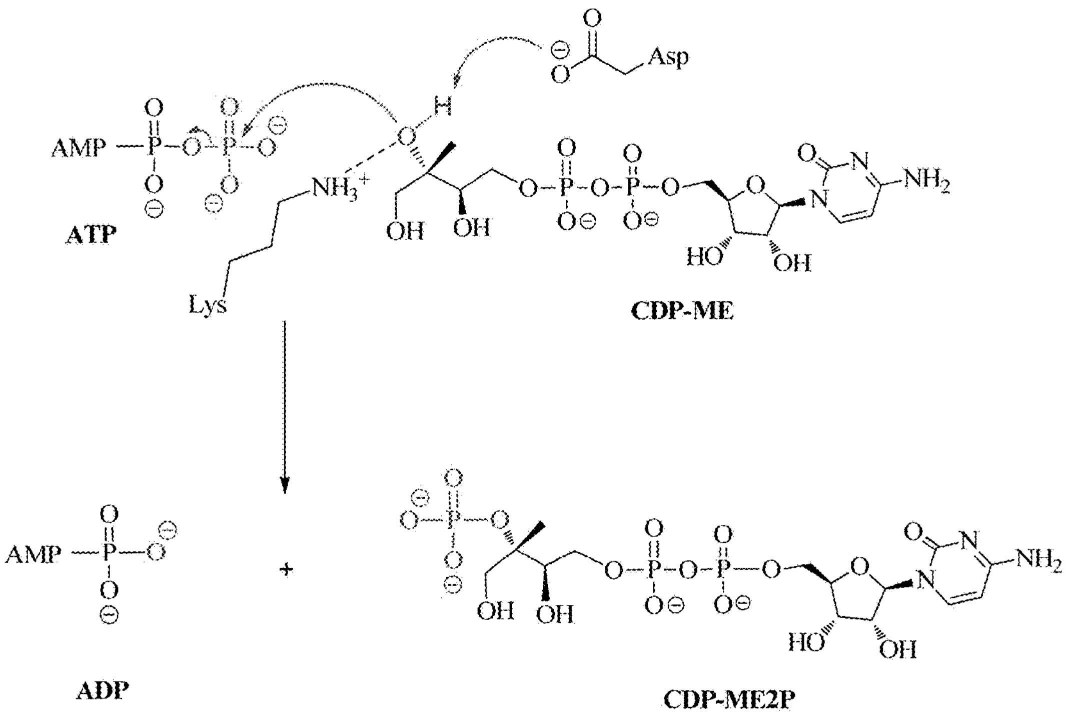
FIG. 1 shows a representative proposed mechanism for IspE catalysis.

Compounds with the capacity to inhibit the biosynthesis of isoprenoids have been discovered and are described hereinbelow.

Isoprenoids are one of the most diverse sets of compounds that are vital for all living organisms. Isoprenoids and their precursors are synthesized by either the mevalonic acid (MVA) pathway or the methylerythritol phosphate (MEP) pathway. Several pathogenic bacteria, including *Mycobacterium tuberculosis* (the causative agent of tuberculosis), *B. pseudomallei* (an overlap select agent and causative agent for melioidosis), and *P. aeruginosa* (a causative agent of nosocomial infections particularly in burn victims and an infective agent for cystic fibrosis patients) use the MEP pathway exclusively to synthesize isoprenoids; humans only possess and use the MVA pathway. This metabolic difference may be exploited to develop drugs that selectively disrupt isoprenoid biosynthesis in pathogenic microorganisms with minimal disruption to isoprenoid biosynthesis in humans. In the MEP pathway, seven enzymes are involved in the biosynthesis of two universal isoprenoid precursors: isopentyl pyrophosphate and dimethylallyl pyrophosphate.

The fragment FOL7185 (compound 17) was found to be a hit against IspD and IspE enzymes isolated from bacteria, and a series of analogs containing the pyrazolopyrimidine core were synthesized.

(17)

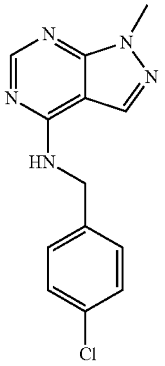

FOL7185

The majority of these compounds inhibited the growth of *Burkholderia thailandensis* (Bt) and *Pseudomonas aeruginosa* (Pa) in the Kirby-Bauer disk diffusion susceptibility test.

Pyrazolopyrimidine compounds in accordance with the present teachings inhibit a unique enzyme pathway that is only found in certain types of infectious disease agents, but not in human beings. Thus, pyrazolopyrimidine compounds in accordance with the present teachings may be used in the treatments of infectious diseases such as malaria and a range of bacterial infections. By way of non-limiting example, as further described below, pyrazolopyrimidine compounds in accordance with the present teachings have shown antibacterial activity against *Burkholderia thailandensis* and *Pseudomonas aeruginosa*.

Materials and methods to design and create different analogs of pyrazolopyrimidine that inhibit the IspE enzymes of the MEP pathway are described below. Embodiments include pyrazolopyrimidine derivatives, compositions containing the pyrazolopyrimidine derivatives, and methods of treatment using therapeutically effective amounts of the optionally substituted pyrazolopyrimidine derivatives. Compounds and compositions in accordance with the present teachings may be used to treat bacterial disease, wherein the bacteria utilize the non-mevalonate pathway, such as *Burkholderia* spp. and *Mycobacterium* spp.

By way of general introduction, a compound in accordance with the present teachings, further described below in reference to specific exemplary compounds, has a general formula (I)

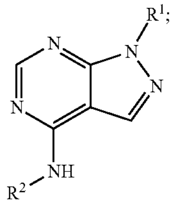

(I)

or a pharmaceutically acceptable salt thereof. In formula (I), $R^1$ includes an alkyl group and $R^2$ includes an optionally substituted moiety selected from the group consisting of an optionally substituted benzyl group, an optionally substituted phenethyl group, an optionally substituted ethanol group, an optionally substituted ethyl acetate group, an optionally substituted methyl furan group, an optionally substituted 3-ethyl indole group, and a lower alkyl group (e.g., iso-propyl). In some embodiments, formula (I) specifically excludes any one of the compounds 3 through 31 shown in Table 1 below and/or described in the Examples and, in other embodiments, formula (I) specifically excludes any combination of two or more of such compounds.

Throughout this description and in the appended claims, the following definitions are to be understood:

The phrase "compounds in accordance with the present teachings" and similar terms and phrases refer to an IspE inhibitor compound of a type described herein, a compound of formula (I), a compound shown in Table 1 below, and/or a compound described in the Examples—in addition to any pharmaceutically acceptable salts, solvates, clathrates, hydrates, polymorphs and/or prodrugs thereof.

Compounds in accordance with the present teachings may contain one or more chiral centers and/or double bonds and, therefore, exist as stereoisomers, such as double-bond isomers (i.e., geometric isomers), enantiomers, or diastereomers. In accordance with the present teachings, the chemical structures depicted herein, including the compounds of this disclosure, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric, and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds in accordance with the present teachings may be preferred.

The term "alkyl" refers to a substituted or unsubstituted, straight, branched or cyclic saturated hydrocarbon radical containing, in some embodiments, from 1 to 10 carbon atoms. Representative examples of unsubstituted alkyl groups in accordance with the present teachings include but are not limited to methyl, ethyl, propyl, iso-propyl, cyclopropyl, butyl, iso-butyl, tert-butyl, sec-butyl, cyclobutyl, and the like. In some embodiments, alkyl has from 1 to 8 carbon atoms. In other embodiments, alkyl has from 1 to 6 carbon atoms. In further embodiments, alkyl has from 1 to 4 carbon atoms. In some embodiments, alkyl has 1 carbon (i.e., methyl). The alkyl group may optionally be substituted with one or more substituents such as fluorine, chlorine, alkoxy groups having from 1 to 8 carbon atoms (e.g., methoxy or ethoxy), or amido groups having from 1 to 8 carbon atoms, such as acetamido. These substituents may themselves be substituted with one or more functional groups such as hydroxy groups, carboxy groups, acetoxy groups, or halogens.

The term "lower" refers to a group having up to four atoms. For example, a "lower alkyl" refers to an alkyl radical having from 1 to 4 carbon atoms. Included in this definition is a lower group having 1 to 2 carbon atoms and a lower group having 1 to 3 carbon atoms.

The term "halo" refers to fluorine, chlorine, iodine or bromine.

The term "substituted" refers to the optional attachment of one or more substituents onto a backbone structure (e.g., an alkyl backbone, the phenyl portion of a benzyl group, the phenyl portion of a phenethyl group, the five-membered pyrazole portion of a pyrazolopyrimidine backbone, the six-membered pyrimidine portion of a pyrazolopyrimidine backbone, alkyl groups that link the $R^2$ moiety to the 4-amino group attached to the pyrimidine portion of a pyrazolopyrimidine backbone, etc.). Representative substituents for use in accordance with the present teachings include but are not limited to alkyl, alkenyl, alkynyl, aryl, heteroaryl, heterocyclyl, cycloalkyl, thio, alkoxy, halo, hydroxy, cyano, nitro, amino (—$NH_2$, —$NHR^a$, —$NR^aR^b$), oxy (—O—), carboxyl (—CO—), $SO_3H$, perfluoroalkyl, perfluoroalkoxy, methylenedioxy, ethylenedioxy, oxo, thioxo, imino (alkyl, aryl, aralkyl), $S(O)_n$ alkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), and the like. These substituents may optionally be further substituted with 1-3 substituents. Examples of substituted substituents include but are not limited to carboxamide, haloalkyl, and the like.

The term "polymorph" refers to solid crystalline forms of a compound or complex thereof. Different polymorphs of the same compound may exhibit different physical, chemical and/or spectroscopic properties. Different physical properties include but are not limited to stability (e.g., to heat or light), compressibility and density (important in formulation and product manufacturing), and dissolution rates (which may affect bioavailability). Differences in stability may result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs may affect their processing. For example, one polymorph might be more likely to form solvates or might be more difficult to filter or wash free of impurities than another due to, for example, the shape or size distribution of particles of it.

The term "antibacterial" refers to compounds or compositions in accordance with the present teachings that have either bactericidal or bacteriostatic activity. An "antibacterial" compound or composition in this context may inhibit the growth of *Pseudomonas aeruginosa, Burkholderia thailandensis* and/or other *Burkholderia* spp. (e.g., *Burkholderia pseudomallei*), and/or other gram-negative bacteria. Additionally, an antibacterial compound or composition in accordance with the present teachings may inhibit the growth of *Mycobacterium tuberculosis* and/or other *Myco-*

*bacterium* spp. The phrase “inhibiting the growth” indicates that the rate of increase in the numbers of a population of particular bacteria is reduced. Thus, the term includes situations in which the bacterial population increases but at a reduced rate, as well as situations where the growth of the population is stopped, as well as situations where the numbers of the bacteria in the population are reduced or the population even eliminated.

The phrase “antimicrobial agent” refers to a substance that kills microbes or inhibits microbial growth or replication. Microbes are microorganisms that include bacteria, fungi, or protozoans. An antimicrobial agent may be an antibiotic (e.g., streptomycin) or may be a non-pharmaceutical antimicrobial (e.g., chlorhexidine, silver, triclosan).

The terms “treat” and “treatment” refer to therapeutic treatment, wherein the object is to inhibit or slow down (lessen) an undesired physiological change or disorder, such as the development or spread of infection. For purposes of the present teachings, beneficial or desired clinical results include but are not limited to alleviation of symptoms, diminishment of extent of disease, stabilized (i.e., not worsening) state of disease, delay or slowing of disease progression, amelioration, and/or palliation of the disease state. The term “treatment” may also refer to prolonging survival as compared to expected survival in the absence of treatment. Those in need of treatment include those already with the condition or disorder as well as those prone to developing the condition or disorder and/or those in which the condition or disorder is to be prevented.

The term “patient” used in reference to the recipient of treatment or therapy refers to any animal classified as a mammal, including humans, domestic and farm animals, and zoo, sports, or pet animals, such as dogs, horses, cats, cows, and the like. In some embodiments, the patient is human.

In some embodiments, the $R^1$ moiety in formula (I) includes a lower alkyl group which, in some embodiments, is selected from the group consisting of methyl, ethyl, n-propyl, iso-propyl, n-butyl, sec-butyl, tert-butyl, and iso-butyl. In some embodiments, $R^1$ (I) in formula is methyl.

As noted above, the $R^2$ moiety in formula (I) may be optionally substituted with one or a plurality of substituents. In some embodiments, an optionally substituted benzyl group in accordance with the present teachings is an optionally substituted group of formula (II):

(II)

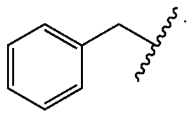

In some embodiments, an optionally substituted phenethyl group in accordance with the present teachings is an optionally substituted group of formula (III)

(III)

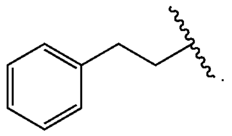

In some embodiments, an optionally substituted ethanol group in accordance with the present teachings is an optionally substituted group of formula (IV)

(IV)

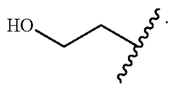

In some embodiments, an optionally substituted ethyl acetate group in accordance with the present teachings is an optionally substituted group of formula (V)

(V)

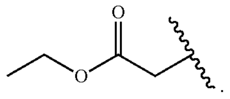

In some embodiments, an optionally substituted methyl furan group in accordance with the present teachings is an optionally substituted group of formula (VI)

(VI)

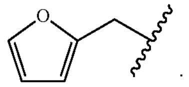

In some embodiments, an optionally substituted 3-ethyl indole group in accordance with the present teachings is an optionally substituted group of formula (VII)

(VII)

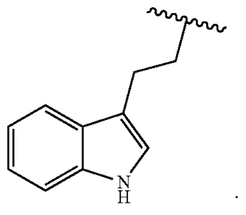

In some embodiments, when $R^2$ is a lower alkyl group, the lower alkyl group is iso-propyl.

In some embodiments, the $R^2$ moiety includes one or a plurality of substituents which, in some embodiments, are electron-withdrawing substituents. Representative electron-withdrawing substituents for use in accordance with the present teachings include but are not limited to halo and nitro. In some embodiments, representative electron-withdrawing substituents are selected from the group consisting of fluoro, chloro, nitro, and combinations thereof.

In some embodiments, the $R^1$ moiety in formula (I) is methyl or tert-butyl, and the $R^2$ moiety includes the optionally substituted benzyl group of formula (II), the optionally substituted phenyethyl group of formula (III), or the optionally substituted methyl furan group of formula (VI). In some embodiments, the phenyl ring of the phenethyl group of formula (III), the phenyl ring of the benzyl group of formula (II), or the furan ring of the methyl furan group of formula (VI) includes one or a plurality of electron-withdrawing substituents and, in some embodiments, two or more electron-withdrawing substituents. In some embodiments, each of the two or more electron-withdrawing substituents is independently selected from the group consisting of fluoro, chloro, and nitro.

In some embodiments, the $R^1$ moiety in formula (I) is tert-butyl and the $R^2$ moiety is unsubstituted methyl furan, such that the compound of formula (I) corresponds to compound 8 in Table 1.

In some embodiments, the $R^1$ moiety in formula (I) is tert-butyl and the $R^2$ moiety is unsubstituted benzyl, such that the compound of formula (I) corresponds to compound 11 in Table 1.

In some embodiments, the $R^1$ moiety in formula (I) is tert-butyl and the $R^2$ moiety includes the benzyl group of formula (II) substituted with a nitro group at its 3-position, such that the compound of formula (I) corresponds to compound 15 in Table 1.

In some embodiments, the $R^1$ moiety in formula (I) is methyl and the $R^2$ moiety includes the benzyl group of formula (II) di-substituted with chlorine atoms at its 3- and 4-positions, such that the compound of formula (I) corresponds to compound 18 in Table 1.

In some embodiments, the $R^1$ moiety in formula (I) is tert-butyl and the $R^2$ moiety includes the benzyl group of formula (II) di-substituted with chlorine atoms at its 3- and 4-positions, such that the compound of formula (I) corresponds to compound 19 in Table 1.

In some embodiments, the $R^1$ moiety in formula (I) is methyl and the $R^2$ moiety includes the phenethyl group of formula (III) substituted with a fluorine atom at its 2-position, such that the compound of formula (I) corresponds to compound 21 in Table 1.

In some embodiments, the $R^1$ moiety in formula (I) is methyl and the $R^2$ moiety includes the phenethyl group of formula (III) substituted with a chlorine atom at its 2-position and a fluorine atom at its 6-position, such that the compound of formula (I) corresponds to compound 26 in Table 1.

In some embodiments, the $R^1$ moiety in formula (I) is methyl and the $R^2$ moiety in formula (I) has a formula (VIII)

(VIII)

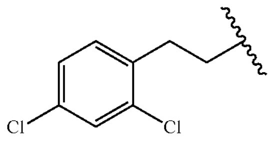

, such that the compound of formula (I) corresponds to the compound 29 further described below.

Compound 29, shown in Table 1 below, exhibits inhibitory activity at 0.1 mM (32.2 μg/mL), which is comparable to the control compound kanamycin (48.5 μg/mL). Compound 29 also shows inhibitory activity at 0.5 mM against kanamycin resistant *P. aeruginosa*. Saturation transfer difference NMR (STD-NMR) screening of these compounds against BtIspD and BtIspE indicated that most of these compounds significantly interact with BtIspE, suggesting that the compounds may inhibit the growth of Bt by disrupting isoprenoid biosynthesis. Ligand epitope mapping of compound 29 with BtIspE indicated that hydrogens on 2,4-dichlorophenyl group have higher proximity to the surface of the enzyme than hydrogens on the pyrazolopyrimidine ring.

In accordance with the present teachings, inhibitors towards IspE and other enzymes in the MEP pathway are developed, which utilize cytidine nucleotide derivatives in driving reactions forward. IspE is the fourth enzyme in the MEP pathway, and is responsible for transferring a terminal phosphate group from adenosine triphosphate (ATP) to cytidine diphosphate 2C-methyl-D-erythritol (CDP-ME) to form 4-diphosphocytidyl-2C-methyl-D-erythritol-2-phosphate (CDP-ME2P) as shown in FIG. 1

Previous work by the Seattle Structural Genomics Center for Infectious Disease (SSGCID) demonstrated the utility of saturation transfer difference (STD) NMR-based fragment screening to find chemical starting points for *B. pseudomallei* (Bp) IspF. In collaboration with the SSGCID, additional NMR-based screening campaigns were conducted against *Mycobacterium* paratuberculosis (Mp) IspD, *Mycobacterium abscessus* (Ma) IspE and BpIspF with approximately 1000 compounds. From this effort, FOL7185 (compound 17) was identified as a clear fragment binder for both MpIspD and MaIspE, and a very weak binder below the STD-NMR hit threshold for BpIspF.

Figure 2:
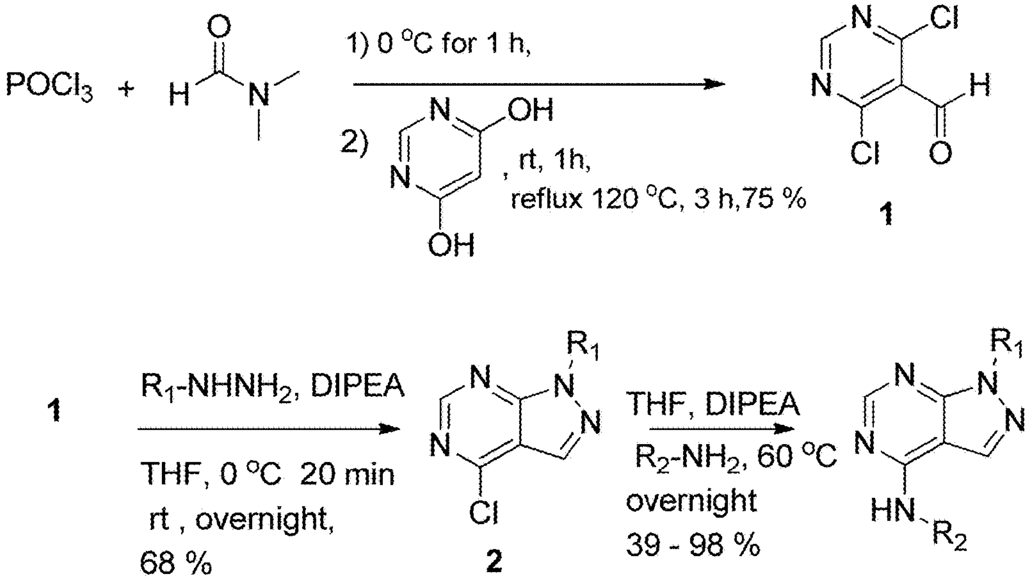
FIG. 2 shows a representative chemical synthesis of pyrazolopyrimidine derivatives.

Following up this initial hit, a series of closely related analogs were designed, and synthesized in four steps as shown in FIG. 2.

In the first step, the reaction between phosphorus oxychloride and dimethylformamide generates iminium salt in situ which is known as the Vilsmeier-Haack reagent. Reaction of the iminium salt with 4,6-dihydroxylpyrimidne followed by hydrolysis afforded the formylating product 1. Consequently, reaction of 4,6-dichloropyrimidine-5-carbaldehyde with methyl or tertiary butyl hydrazine gave a monochloro-substituted pyrazolopyrimidine core 2, which was then reacted with different primary amines to afford the target compounds (Examples 4-33).

Zone of inhibition assays were conducted for each compound against two closely related bacteria, *B. thailandensis* and *P. aeruginosa*, both of which use the MEP pathway to synthesize isoprenoids. Assay data was acquired at 1.0 mM and 0.5 mM, plus 0.1 mM concentration points for each compounds (Table 1).

TABLE 1
| Zone of inhibition assay of pyrazolopyrimidines against *B. thailandensis* and *P. aeruginosa*. | | | | | |
|---|---|---|---|---|---|
| 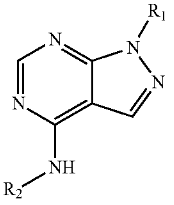 | | | Zone of inhibition (diameter, in millimeter) | | |
| No | $R_1$ | $R_2$ | Conc. (in mM) | *B. thailandensis* | *P. aeruginosa* |
| 3 | $—CH_3$ | 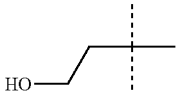 | 0.1 | 0 | 0 |
| | | | 0.5 | 0 | 15 |
| | | | 1.0 | 0 | 21 |
| 4 | $—CH_3$ | 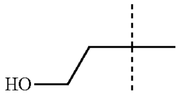 | 0.1 | 0 | 0 |
| | | | 0.5 | 8 | 12 |
| | | | 1.0 | 12 | 20 |
| 5 | $—CH_3$ | 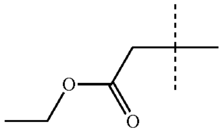 | 0.1 | 0 | 0 |
| | | | 0.5 | 8 | 0 |
| | | | 1.0 | 12 | 13 |
| 6 | $—CH_3$ | 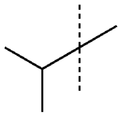 | 0.1 | 0 | 0 |
| | | | 0.5 | 13 | 0 |
| | | | 1.0 | 21 | 10 |
| 7 | $—CH_3$ | 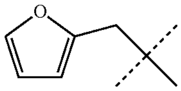 | 0.1 | 0 | 0 |
| | | | 0.5 | 0 | 0 |
| | | | 1.0 | 20 | 0 |
| 8 | $—C(CH_3)_3$ | 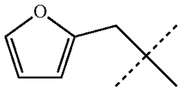 | 0.1 | 0 | 0 |
| | | | 0.5 | 12 | 6 |
| | | | 1.0 | 14 | 12 |
| 9 | $—CH_3$ | 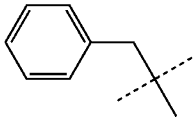 | 0.1 | 0 | 0 |
| | | | 0.5 | 0 | 0 |
| | | | 1.0 | 12 | 0 |
| 10 | $—CH_3$ | 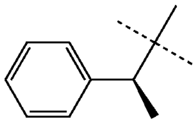 | 0.1 | 0 | 0 |
| | | | 0.5 | 11 | 8 |
| | | | 1.0 | 19 | 14 |
| 11 | $—C(CH_3)_3$ | 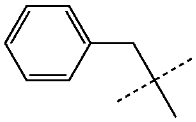 | 0.1 | 0 | 0 |
| | | | 0.5 | 12 | 0 |
| | | | 1.0 | 18 | 0 |
| 13 | $—CH_3$ | 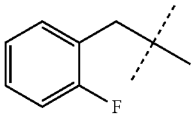 | 0.1 | 0 | 0 |
| | | | 0.5 | 8 | 12 |
| | | | 1.0 | 13 | 18 |

TABLE 1-continued

Zone of inhibition assay of pyrazolopyrimidines against *B. thailandensis* and *P. aeruginosa.*

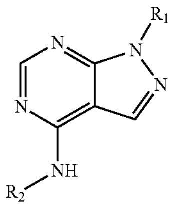

| No | $R_1$ | $R_2$ | Conc. (in mM) | Zone of inhibition (diameter, in millimeter) *B. thailandensis* | *P. aeruginosa* |
|---|---|---|---|---|---|
| 14 | —$CH_3$ | 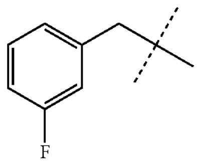 | 0.1<br>0.5<br>1.0 | 0<br>6<br>11 | 0<br>10<br>15 |
| 15 | —$C(CH_3)_3$ | 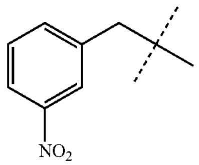 | 0.1<br>0.5<br>1.0 | 0<br>12<br>16 | 0<br>13<br>17 |
| 16 | —$CH_3$ | 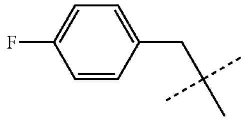 | 0.1<br>0.5<br>1.0 | 0<br>9<br>18 | 0<br>12<br>18 |
| 17 (FOL7185) | —$CH_3$ | 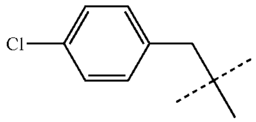 | 0.1<br>0.5<br>1.0 | 0<br>0<br>0 | 0<br>0<br>0 |
| 18 | —$CH_3$ | 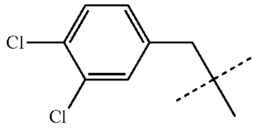 | 0.1<br>0.5<br>1.0 | 0<br>12<br>18 | 0<br>10<br>20 |
| 19 | —$C(CH_3)_3$ | 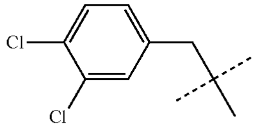 | 0.1<br>0.5<br>1.0 | 0<br>16<br>20 | 0<br>12<br>16 |
| 20 | —$CH_3$ | 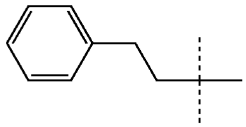 | 0.1<br>0.5<br>1.0 | 0<br>9<br>20 | 0<br>0<br>0 |
| 21 | —$CH_3$ | 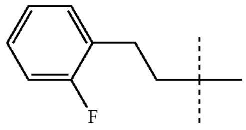 | 0.1<br>0.5<br>1.0 | 0<br>12<br>16 | 0<br>8<br>16 |
| 22 | —$CH_3$ | 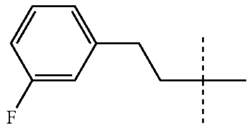 | 0.1<br>0.5<br>1.0 | 0<br>11<br>14 | 0<br>0<br>8 |

TABLE 1-continued

Zone of inhibition assay of pyrazolopyrimidines against *B. thailandensis* and *P. aeruginosa.*

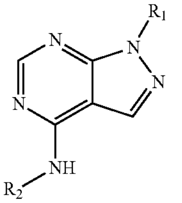

| No | $R_1$ | $R_2$ | Zone of inhibition (diameter, in millimeter) | | |
|---|---|---|---|---|---|
| | | | Conc. (in mM) | *B. thailandensis* | *P. aeruginosa* |
| 23 | $—CH_3$ | 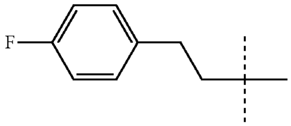 | 0.1<br>0.5<br>1.0 | 0<br>12<br>22 | 0<br>9<br>17 |
| 24 | $—CH_3$ | 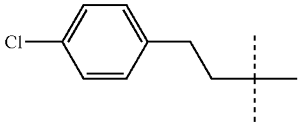 | 0.1<br>0.5<br>1.0 | 0<br>10<br>13 | 0<br>0<br>10 |
| 25 | $—CH_3$ | 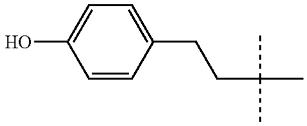 | 0.1<br>0.5<br>1.0 | 0<br>0<br>0 | 0<br>0<br>0 |
| 26 | $—CH_3$ | 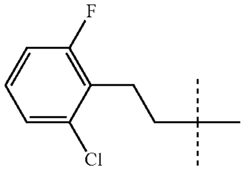 | 0.1<br>0.5<br>1.0 | 0<br>13<br>21 | 0<br>11<br>19 |
| 27 | $—C(CH_3)_3$ | 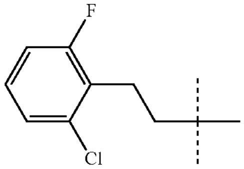 | 0.1<br>0.5<br>1.0 | 0<br>12<br>16 | 0<br>0<br>0 |
| 28 | $—C(CH_3)_3$ | 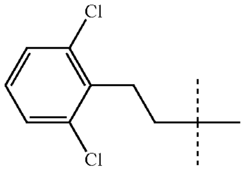 | 0.1<br>0.5<br>1.0 | 0<br>11<br>18 | 0<br>0<br>0 |
| 29 | $—CH_3$ | 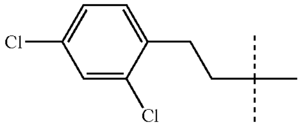 | 0.1<br>0.5<br>1.0 | 6<br>10<br>18 | 0<br>12<br>18 |
| 30 | $—CH_3$ | 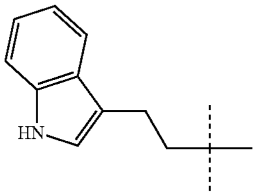 | 0.1<br>0.5<br>1.0 | 0<br>12<br>14 | 0<br>0<br>0 |

TABLE 1-continued

Zone of inhibition assay of pyrazolopyrimidines against *B. thailandensis* and *P. aeruginosa.*

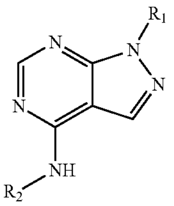

| No | $R_1$ | $R_2$ | Zone of inhibition (diameter, in millimeter) Conc. (in mM) | *B. thailandensis* | *P. aeruginosa* |
|---|---|---|---|---|---|
| | Kanamycin (positive control) | | 0.1 | 6 | 0 |
| | | | 0.5 | 22 | 0 |
| | | | 1.0 | 30 | 0 |

Although the fragment hit FOL7185 did not show inhibition in this assay, the majority of the synthesized analogs (3-29) were active against *B. thailandensis* (E264), with fewer compounds demonstrating inhibition with *P. aeruginosa* (ATCC 27853). ATCC 27853 strain is resistant to kanamycin, and the smaller number of active compounds is most likely related to the intrinsic resistance development of the bacterium. Fluorobenzyl and 3,4-dichlorobenzyl compounds showed comparable potency against both *B. thailandensis* and *P. aeruginosa*. Activity was not detected for the 4-hydroxylphenethyl substituent 25. While neither desiring to be bound by any particular theory nor intending to limit in any measure the scope of the appended claims or their equivalents, it is presently believed that electron withdrawing groups such as chloro, fluoro and nitro groups may be important for biological activity. Moreover, a subtle difference was observed with 2- and 4-fluorophenethyl compounds (21 and 23) versus 3-fluorophenethyl 22 against *B. thailandensis* and *P. aeruginosa*. While neither desiring to be bound by any particular theory nor intending to limit in any measure the scope of the appended claims or their equivalents, it is presently believed that lipophilic electron withdrawing groups at the 2 and 4 positions on the phenethyl group may result in increased potency. Compound 29 was subsequently designed and synthesized, containing 2,4-dichloro substituents on the phenethyl group. This compound showed inhibitory activity against *B. thailandensis* when tested at 0.1 mM (32.2 μg/mL), comparable to results obtained with kanamycin (48.5 μg/mL).

To help validate target specificity, compounds were tested by STD-NMR for binding to IspD and IspE from *B. thailandensis*, using similar conditions as that of the primary fragment screen. STD-NMR data for these compounds was acquired before and after the addition of competitive binders, to test for binding site specificity on each protein. Data for BtIspD was acquired before and after addition of 2 molar equivalents of cytidine diphosphate (CDP) per compound. Data for BtIspE was acquired before and after addition of 2 molar equivalents of adenosine diphosphate (ADP), followed by 2× addition of CDP, relative to the compound, to efficiently probe two sites on the kinase.

Figure 3:
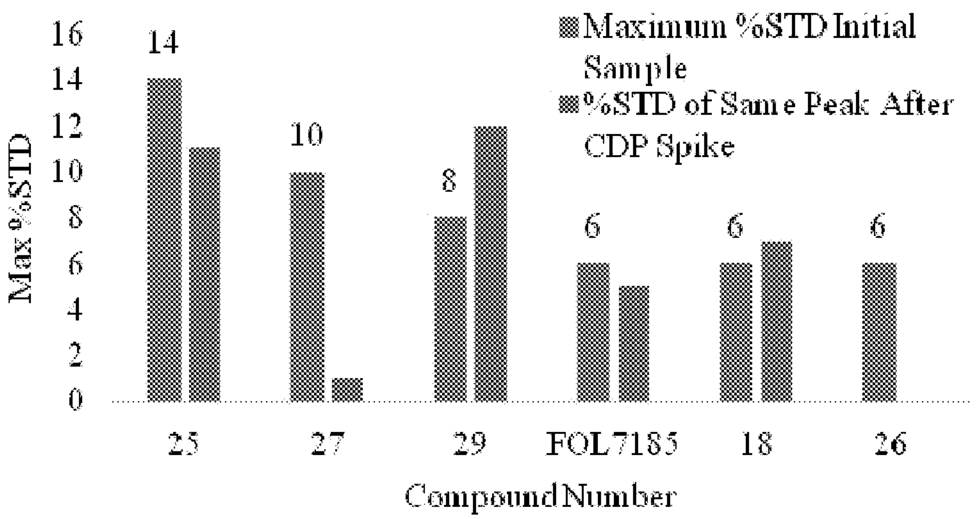
FIG. 3 shows a bar graph for pyrazolopyrimidine compounds with measurable % STD binding against BtIspD before and after addition of CDP.

Most of the compounds tested showed weak (<10%) STD binding signal against BtIspD. The strongest binders to BtIspD by STD-NMR include compounds 18, 25, 26, 27, 29 and the original screening hit FOL7185 (FIG. 3). Addition of CDP shows a large decrease in STD binding for compounds 26 and 27. This is indicative of competitive binding at the same site on BtIspD, for compounds with affinities near or below that of CDP. The remainder of compounds with measurable binding by STD showed no significant change upon addition of CDP. It is possible that no change in STD is due to binding in an alternative site on the protein. However, given the structural similarities between all compounds tested, it is more likely the case that 2× molar excess of CDP is insufficient to quench STD binding for these compounds at the same site of the protein.

Figure 4:
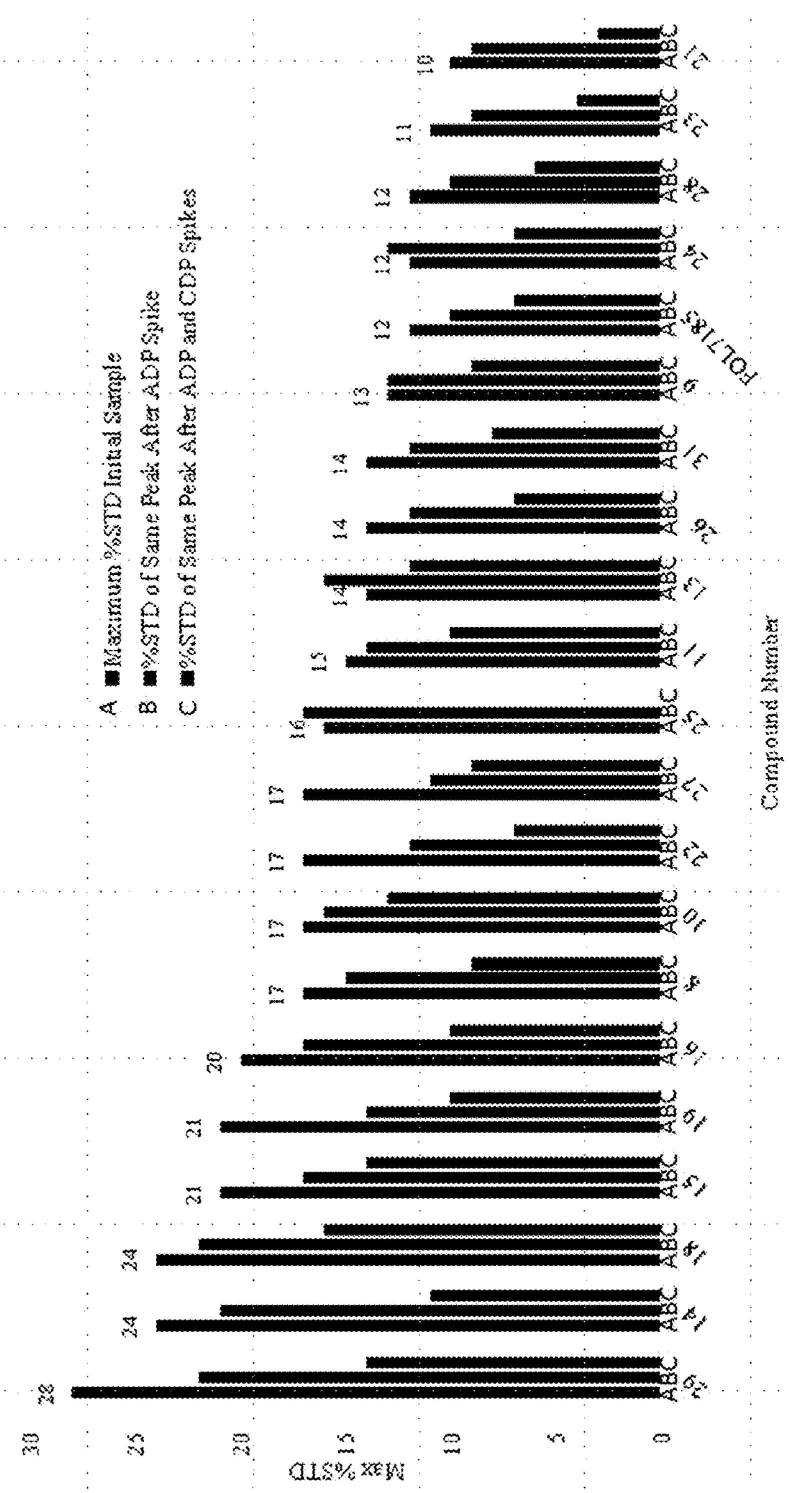
FIG. 4 shows a bar graph of pyrazolopyrimidine compounds with % STD≥10 against BtIspE before and after addition of ADP and CDP.
Figure 5:
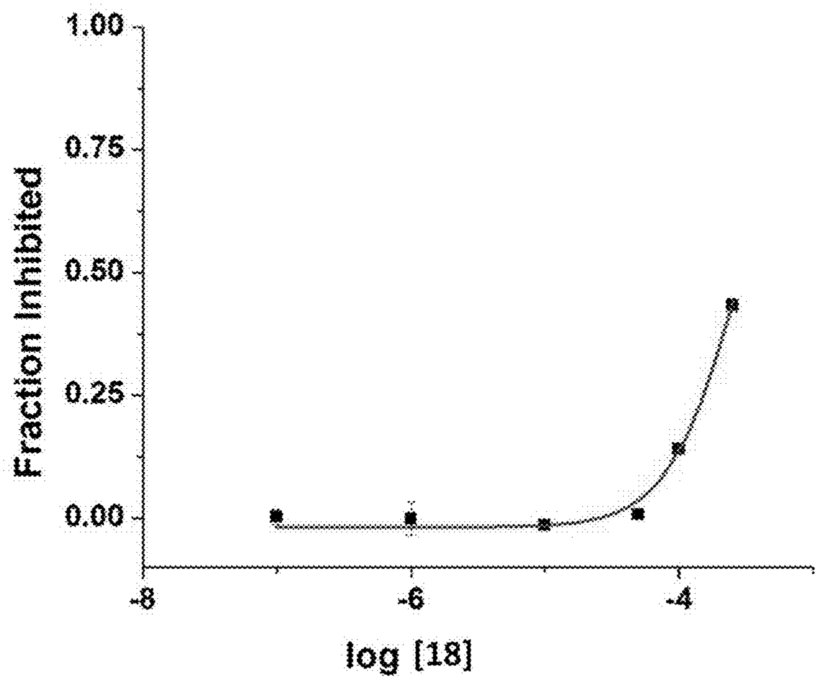
FIG. 5 shows a dose response curve for compound 18 for Bt IspE.
Figure 6:
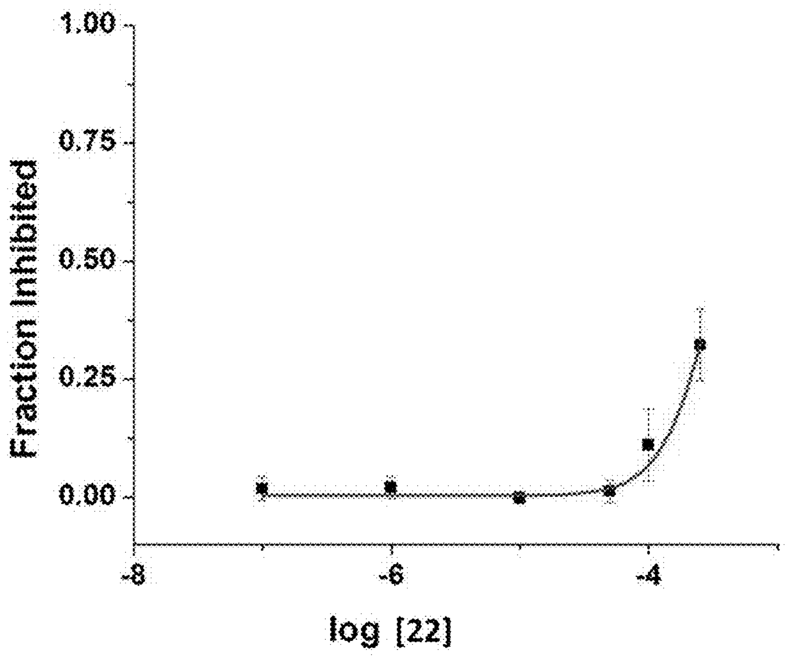
FIG. 6 shows a dose response curve for compound 22 for Bt IspE.
Figure 7:
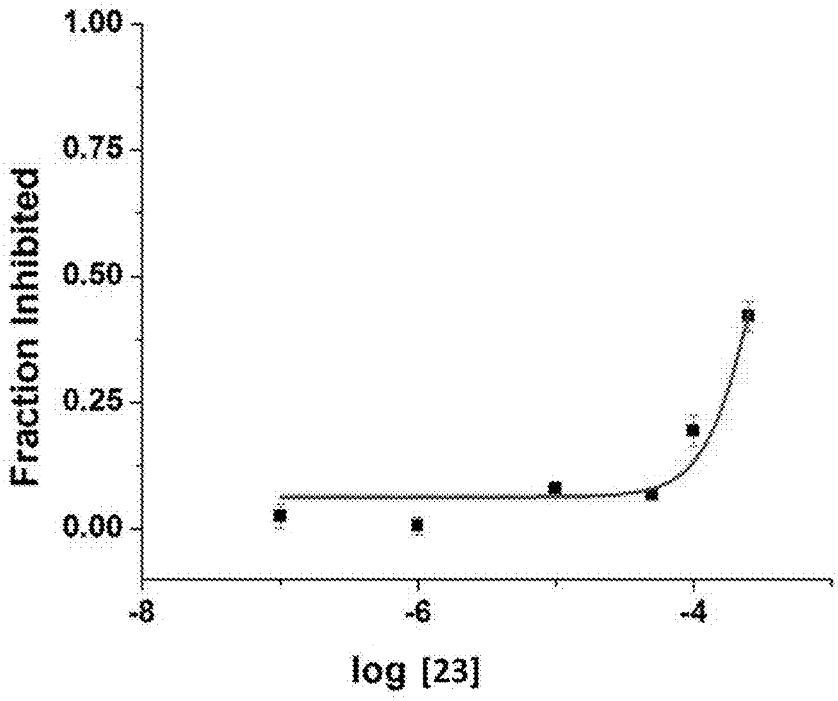
FIG. 7 shows a dose response curve for compound 23 for Ec IspE.
Figure 8:
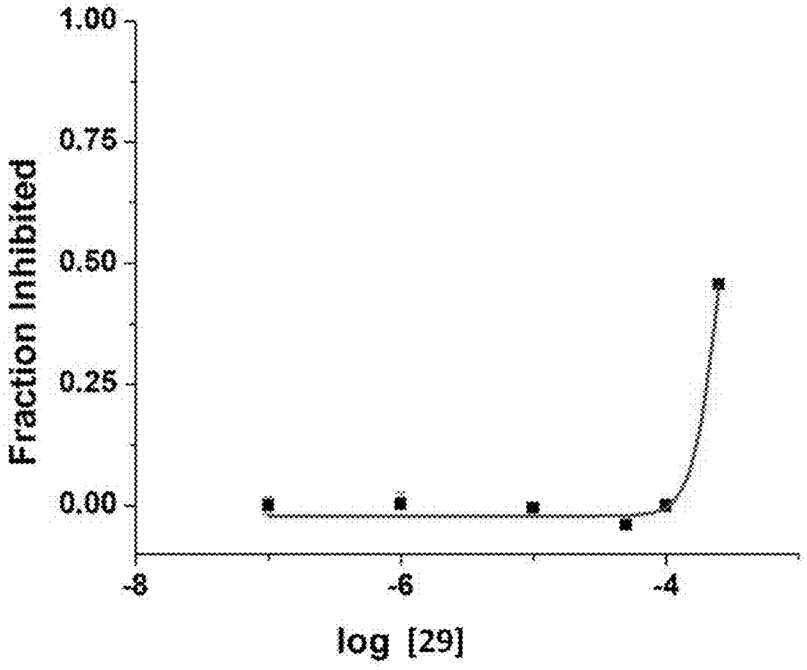
FIG. 8 shows a dose response curve for compound 29 for Bt IspE.

The majority of the pyrazolopyrimidines that were active in the zone of inhibition assay showed significant binding with BtIspE by STD-NMR (FIG. 4). Overall, there was very little decrease in STD binding signal after addition of ADP, while the subsequent addition of CDP tended to cause a greater decrease. Given the similarity in chemical structure for all compounds tested and their binding behavior with IspD, these results suggest that the compounds are preferentially binding to the substrate site of BtIspE, over that of the ATP co-factor. However, it is difficult to deconvolute contributions to STD binding signal which may arise from compounds binding both sites. The % STD binding signal of compound 25 experiences no change upon addition of ADP, but loses all binding signal entirely after the addition of CDP (FIG. 4). Compound 25 did not show zone of inhibition activity against *B. thailandensis* and *P. aeruginosa* at the concentrations tested, which correlates with weaker binder by % STD. Hence it is most likely that compounds in this series binding to both BtIspD and BtIspE at the substrate binding site.

Some compounds that have high % STD values in binding to BtIspE, such as 29, 14, and 18, contain methyl groups at the $R^1$ position. While neither desiring to be bound by any particular theory nor intending to limit in any measure the scope of the appended claims or their equivalents, it is presently believed that sterically-demanding groups may have unfavorable interactions with the enzyme, or may somehow disrupt interactions between the enzyme and the pyrazolopyrimidine core. These compounds also have halo/dihalo benzyl or phenethyl groups at the $R^2$ position, suggesting a potential hydrophobic or π-π stacking interactions could enhance binding with BtIspE. While neither desiring to be bound by any particular theory nor intending to limit in any measure the scope of the appended claims or their equivalents, it is presently believed that the halo/dihalo benzyl or phenethyl groups at the $R^2$ position may also play an important role by properly orienting the pyrazolopyrimidine core to interact with the cytidine binding pocket. These traits are highlighted by compound 29, which displays the highest % STD value of any compounds against BtIspE, and is the most potent compound tested against *B. thailandensis* in zone of inhibition assays (32.2 μg/mL).

To determine the relative proximity of the hydrogen atoms of compound 29 to the surface of BtIspE when bound, STD-NMR data were collected for the compound in the presence of enzyme across a range of saturation times (0.5 to 5.0 seconds). STD amplification factors were then calculated for each well-resolved proton resonance. STD build-up curves were generated for each resolvable proton, and the slopes of each curve were calculated and normalized to STD-fit values, to estimate the relative proximity of each hydrogen atom to the surface of the enzyme when bound. The binding epitope data indicate that the H6', H3', and H5' hydrogen atoms of compound 29 experience more saturation transfer during the experiment than H3, H6 and methyl hydrogens (Table 2, compound 29).

29

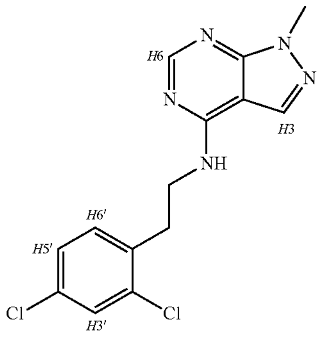

This result suggests that the 2,4-dichlorophenyl moiety is the most deeply buried, and/or has the most favorable or complementary contact with the protein when compound 29 is bound.

TABLE 2

STD-fit values of compound 29 hydrogens.

| Hydrogen | Slope | STD-fit |
|---|---|---|
| H6' | 1.49 | 100 |
| H5' | 1.33 | 90 |
| H3' | 1.47 | 99 |
| H3 | 1.00 | 67 |
| H6 | 0.79 | 53 |
| Methyl | 0.55 | 37 |

In summary, FOL 7185 was used as a template to design a number of pyrazolopyrimidine analogs for testing with BtIspD and BtIspE. Although FOL7185 did not show measurable growth inhibition against *B. thailandensis* and *P. aeruginosa* in the zone of inhibition assay, a number of its analogs did show growth inhibition. Most notably, compound 29 was found to inhibit *B. thailandensis* at 0.1 mM concentration, which is comparable to kanamycin. This compound also showed measurable potency against a multi-drug resistant strain of *P. aeruginosa*, thus demonstrating cross-species inhibition and potential as a starting point for broad-spectrum antibiotic activity. In STD-NMR studies, compound 29 shows significant interactions with the active site of BtIspE, suggesting that these analogs may inhibit bacterial growth by disrupting isoprenoid biosynthesis. The high potency of compound 29 appears to be caused by low steric interactions at the R1 position of the molecule, and is aided by favorable lipophilic interactions with the 2,4-dichlorophenyl group at $R^2$ position.

Although it is possible for compounds in accordance with the present teachings to be administered to a patient alone in a unit dosage form, compounds are typically administered in admixture with a carrier as a pharmaceutical composition to provide a unit dosage form. A pharmaceutical composition in accordance with the present teachings includes a pharmaceutically acceptable carrier in combination with a compound in accordance with the present teachings or a pharmaceutically acceptable salt thereof.

Representative pharmaceutically acceptable carrier for use in accordance with the present teachings include but are not limited to, physiological saline, ringers, phosphate-buffered saline, and other carriers known in the art. Pharmaceutical compositions in accordance with the present teachings may also include additives such as, for example, stabilizers, antioxidants, colorants, excipients, binders, thickeners, dispersing agents, readsorpotion enhancers, buffers, surfactants, preservatives, emulsifiers, isotonizing agents, and diluents. Pharmaceutically acceptable carriers and additives in accordance with the present teachings may be chosen such that side effects from the pharmaceutical compound are minim/zed and the performance of the compound is not canceled or inhibited to such an extent that treatment is ineffective.

Methods of preparing pharmaceutical compositions containing a pharmaceutically acceptable carrier in combination with a therapeutic compound or a pharmaceutically acceptable acid addition salt of a compound are known to those of skill in the art. The disclosure also includes pharmaceutically acceptable salts of the compounds. The compounds of the disclosure are capable of forming both pharmaceutically acceptable acid addition and/or base salts.

All methods may include the step of bringing one of the compounds in accordance with the present teachings in association with a carrier and one or more additives. Formulations generally are prepared by uniformly and intimately bringing a compound into association with a liquid carrier or a finely divided solid carrier or both, and then, if necessary, shaping the product into the desired unit dosage forms.

As used herein, the term "pharmaceutically acceptable carrier" refers to a non-toxic, inert solid, semi-solid or liquid filler, diluent, encapsulating material or formulation auxiliary of any type.

Liquid dosage forms for oral administration include but are not limited to pharmaceutically acceptable emulsions, microemulsions, solutions, suspensions, syrups and elixirs.

Injectable preparations (e.g., sterile injectable aqueous or oleaginous suspensions) may be formulated according to the known art using suitable dispersing or wetting agents and suspending agents.

In order to prolong the effect of a drug, it is often desirable to slow the absorption of the drug from subcutaneous or intramuscular injection. In some embodiments, this may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release may be controlled. Examples of other biodegradable polymers include but are not limited to poly(orthoesters) and poly(anhydrides). Depot injectable formulations may also be prepared by entrapping the drug in liposomes or microemulsions that are compatible with body tissues.

Solid dosage forms suitable for oral administration in accordance with the present teachings include but are not limited to capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid; (b) binders such as, for example, carboxymethylcellulose, alginates, gelatin, polyvinylpyrrolidinone, sucrose, and acacia; (c) humectants such as glycerol; (d) disintegrating agents such as agar-agar, calcium carbonate, potato or tapioca starch, alginic acid, certain silicates, and sodium carbonate; (e) solution retarding agents such as paraffin; (f) absorption accelerators such as quaternary ammonium compounds; (g) wetting agents such as, for example, acetyl alcohol and glycerol monostearate; (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

The active compounds may also be in micro-encapsulated form with one or more excipients as noted above. The solid dosage forms of tablets, dragees, capsules, pills, and granules may be prepared with coatings and shells such as enteric coatings, release controlling coatings and other coatings well known in the pharmaceutical formulating art. They may optionally contain opacifying agents and may also be of a composition that they release the active ingredient(s) only, or preferentially, in a certain part of the intestinal tract, optionally, in a delayed manner. Examples of embedding compositions that may be used include polymeric substances and waxes.

Dosage forms for topical or transdermal administration of a compound in accordance with the present teachings include but are not limited to ointments, pastes, creams, lotions, gels, powders, solutions, sprays, inhalants or patches.

Compositions may also be formulated for delivery as a liquid aerosol or inhalable dry powder.

The compounds may also be formulated for use as topical powders and sprays that may contain, in addition to the compounds in accordance with the present teachings, excipients such as lactose, talc, silicic acid, aluminum hydroxide, calcium silicates and polyamide powder, or mixtures of these substances.

Transdermal patches have the added advantage of providing controlled delivery of a compound to the body.

According to the methods of treatment in accordance with the present teachings, bacterial infections are treated or prevented in a patient such as a human or lower mammal by administering to the patient a therapeutically effective amount of a compound in accordance with the present teachings, in such amounts and for such time as is necessary to achieve the desired result. By a "therapeutically effective amount" of a compound in accordance with the present teachings is meant a sufficient amount of the compound to treat bacterial or parasitic infections, at a reasonable benefit/risk ratio applicable to any medical treatment. It will be understood, however, that the total daily usage of the compounds and compositions of the present disclosure will be decided by the attending physician within the scope of sound medical judgment. The specific therapeutically effective dose level for any particular patient may depend upon a variety of factors including but not limited to the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

As used herein, the term "kit" refers to an assembly of materials that are used in performing a method in accordance with the present teachings. The components of the kit may be provided in packaged combination in the same or in separate containers, depending on their cross-reactivities and stabilities, and in liquid or in solid form. The amounts and proportions of components provided in the kit may be selected so as to provide optimum results for a particular application. While in some embodiments, the components may be provided in separate physical forms (e.g., one or more solids and one or more fluids), it is to be understood that in other embodiments, all of the components that are to be introduced to patient may be provided together in one common physical form (e.g., one solid composition or one fluid).

The components included in kits in accordance with the present teachings may be supplied in all manner of containers such that the activities of the different components are substantially preserved, while the components themselves are not substantially adsorbed or altered by the materials of the container. Suitable containers include but are not limited to ampoules, bottles, test tubes, vials, flasks, syringes, bags and envelopes (e.g., foil-lined), and the like. The containers may be formed of any suitable material including but not limited to glass, organic polymers (e.g., polycarbonate, polystyrene, polyethylene, polypropylene, etc.), ceramic, metal (e.g., aluminum), metal alloys (e.g., steel), cork, and the like. In addition, the containers may contain one or more access ports (e.g., for access via a needle), such as may be provided by a septum. Preferred materials for septa include rubber and polymers including but not limited to, for example, polytetrafluoroethylene of the type sold under the trade name TEFLON by DuPont (Wilmington, Del.). In addition, the containers may contain two or more compartments separated by partitions or membranes that may be removed to allow mixing of the components.

Kits in accordance with the present teachings may also be supplied with other items known in the art and/or which may be desirable from a commercial and user standpoint, including but not limited to instructions for adding the components of the kit to a heat exchange system.

Instructional materials provided with kits in accordance with the present disclosure may be printed (e.g., on paper) and/or supplied in an electronic-readable medium (e.g., floppy disc, CD-ROM, DVD-ROM, zip disc, videotape, audio tape, etc.). Alternatively, instructions may be provided by directing a user to an Internet web site (e.g., specified by the manufacturer or distributor of the kit) and/or via electronic mail, text message, social media, and/or the like, and combinations thereof.

A "daily dose" may be a single tablet or capsule or several tablets or capsules to be taken on a given day.

The kits of the present disclosure may also include, in addition to ISPF inhibitors, one or more additional pharmaceutically active compounds. In some embodiments, the additional compound is another ISPF inhibitor or another compound useful to treat bacterial or parasitic infections. The additional compounds may be administered in the same dosage form as the ISPF inhibitor compound or in different dosage forms. Likewise, the additional compounds may be administered at the same time as the ISPF inhibitor compound(s) or at different times.

*Burkholderia* spp. cause a number of diseases. For instance, *Burkholderia mallei* is the etiologic agent of glanders. While glanders primarily affects horses, humans, dogs, cats, goats, mules, and donkeys may also contract glanders. Glanders often manifests itself as pulmonary infection. In pulmonary infections, pneumonia, pulmonary abscesses, and pleural effusion may occur. Glanders may also be a localized infection of open wounds and of mucus membranes in the eyes, nose, and respiratory tract. *Burkholderia thailandensis* is an opportunistic pathogen that may cause pneumonia and septicemia. *Burkholderia pseudomallei* is the causative agent of melioidosis.

In some embodiments, a compound or composition in accordance with the present teachings may be administered to a subject to treat a *Burkholderia* infection. In some embodiments, compounds and compositions in accordance with the present teachings may be administered to a subject to treat glanders. In some embodiments, a compound or composition in accordance with the present teachings may be administered to a subject concurrently with the administration of at least one of tetracycline, ciprofloxacin, streptomycin, novobiocin, gentamicin, imipenem, ceftrazidime, or a sulfonamide. In some embodiments, compounds and compositions in accordance with the present teachings may be administered to a subject to treat melioidosis.

Multidrug resistant tuberculosis (MDR-TB) and even extensively drug resistant tuberculosis (XDR-TB) have become more prevalent in the last 20 to 40 years. New treatments are sought to battle the rising rates of drug resistant TB cases. *Mycobacterium tuberculosis*, the etiologic agent of tuberculosis, generates isopentenyl pyrophosphate (IPP) and dimethylallyl pyrophosphate (DMAPP) via the non-mevalonate pathway. Thus, *M. tuberculosis* is a target for the compounds and compositions in accordance with the present teachings. Treatment with compounds and compositions as in accordance with the present teachings represent new treatments for tuberculosis. As such, some embodiments include administering a compound or composition as in accordance with the present teachings to a subject with tuberculosis. The treatment with the compounds and compositions in accordance with the present teachings may optionally be administered with at least one of the first line drugs ethambutol, isoniazid, rifampicin, or pyrazinamide. The treatment with the compounds and compositions in accordance with the present teachings may optionally be administered with at least one of the second line drugs an aminoglycoside (e.g., streptomycin, kanamycin, amikacin), a fluoroquinolone (e.g., ciprofloxacin, ofloxacin, sparfloxacin, moxifloxacin, etc.), capreomycin, viomycin, enviomycin, a thioamide (e.g., ethionamide and protionamide), cycloserine, para-aminosalicylic acid, thiacetazone, clofazimine, linezolid, a macrolide (e.g., clarithromycin, azithromycin), or amoxicillin/clavulanate.

Methods of treating bacterial or parasitic infection in accordance with the present teachings include administering a compound or composition as described herein, and optionally further comprising administering at least one other antibacterial agent.

The following examples and representative procedures illustrate features in accordance with the present teachings, and are provided solely by way of illustration. They are not intended to limit the scope of the appended claims or their equivalents.

EXAMPLES

Zone of Inhibition Assay

Kirby-Bauer disc diffusion susceptibility test was conducted for each compound at 1.0 mM, 0.5 mM and 0.1 mM concentrations against *Burkholderia thailandensis* (E 264) and *Pseudomonas aeruginosa* (ATCC 27853). a. The bacteria were grown in LB broth and spread on LB agar plates with cotton swabs[1]. Sterile filter paper discs were placed on the plates with forceps. Depending on the compound they were dissolved in either 5 or 10% of DMSO and added at different concentrations on each disc. The plates were then incubated at 37° C. for 24-48 hours depending on the organism and the diameter of the zone of inhibition was measured.

Protein Expression and Purification for NMR

Recombinant 2C-methyl-D-erythritol-4-phosphate cytidyltransferase (E.C. 2.7.7.60, BtIspD, target database ID: ButhA.00168.a) and 4-diphosphocytidyl-2-C-methyl-D-erythritol kinase (E.C. 2.7.1.148, BtIspE, target database ID: ButhA.00725.a) from *Burkholderia thailandensis* were generated by methods previously described.[3] The full length IspD sequence (residues 1-236) was PCR-amplified from *Burkholderia thailandensis* E264 gDNA using the primers: GGGTCCTGGTTCGATGGTGACCTCCCGACTCTTCG (SEQ ID NO: 1) and CTTGTTCGTGCTGTTTATTAACTGGCGCGCGCCGGATGC (SEQ ID NO: 2). The full length IspE sequence (residues 1-293) was PCR-amplified from *Burkholderia thailandensis* E264 gDNA using the primers: GGGTCCTGGTTCGATGACCGATACGACCCGCTCG (SEQ ID NO: 3) and CTTGTTCGTGCTGTTTATTATGACGCGAAAGCGAAGAGTGGA (SEQ ID NO: 4). Preparative gel electrophoresis was used to isolate the desired band, which was subsequently excised and purified using a gel extraction kit (Zymo Research, Irvine, Calif.). The purified PCR product was treated with T4 DNA polymerase (NEB, Ipswich, Mass., USA) for ligation-independent cloning (LIC) and annealed to a LIC-prepared AVA0421 vector, which contains a T7 promoter and a cleavable N-terminal hexahistidine (6×His) nickel affinity tag (SEQ ID NO: 9). Purified plasmids were transformed and expressed in BL21(DE3)R3 Rosetta Oxford *E. coli* expression strain. Starter cultures of PA-0.5G non-inducing media (Studier 2005 PMID: 15915565) with appropriate antibiotics were grown for 18 h at 25° C. Antibiotics were added to 2 L bottles of sterile ZYP-5052 auto-induction media and the bottles inoculated with overnight cultures. Inoculated bottles were then placed into a LEX bioreactor and cultures grown for 72 h at 20° C. To harvest, the media was centrifuged at 4,000 RCF for 30 min at 4° C. Cell paste was frozen and stored at −80° C. prior to purification. Frozen cells were re-suspended in lysis buffer (25 mM HEPES (pH 7.0), 500 mM NaCl, 5% (v/v) glycerol, 30 mM imidazole, 0.025% (w/v) sodium azide, 0.5% (w/v) CHAPS, 10 mM $MgCl_2$, 1 mM TCEP, 250 ng/mL AEBSF, and 0.05 μg/mL lysozyme) and disrupted on ice for 30 min with a Virtis sonicator using alternating on/off cycles of 15 s. Cell debris was incubated with 20 μL of Benzonase nuclease (25 U/mL) at room temperature for 45 min, and clarified by centrifugation on a Sorvall SLA-1500 at 29,700 RCF for 60 min at 4° C. Protein was purified from clarified cell lysate by immobilized metal affinity chromatography. His Trap FF 5 mL column (GE Healthcare) were equilibrated with binding buffer (25 mM HEPES (pH 7.0), 500 mM NaCl, 5% (v/v) glycerol, 30 mM imidazole, 0.025% (w/v) sodium azide, 1 mM TCEP). The protein was eluted in the same buffer with 250 mM imidazole added. To remove the N-terminal 6×His (SEQ ID NO: 9) His-tagged 3C protease was added (1:50) to the eluted protein, transferred to dialysis tubing (Snake-Skin 10,000 MWCO Pierce 68100) and dialyzed overnight at 4° C. in 4 L of cleavage buffer (25 mM HEPES (pH 7.5), 200 mM NaCl, 5% (w/v) glycerol, 1 mM TCEP and 0.025% sodium azide). To remove 3C protease and any remaining uncleaved protein, protein sample was gravity fed through 5 mL of Ni-NTA hand packed resin. Size exclusion chromatography (SEC) was run on the cleaved protein using a HiLoad 26/60 Superdex 75 column (GE Healthcare) equilibrated in SEC buffer (20 mM HEPES (pH 7.0), 300 mM NaCl, 2 mM DTT, and 5% (w/v) glycerol). Pure fractions were collected and pooled from a single peak in the chromatogram, and concentrated using Amicon Ultra centrifugal filters. The final protein was concentrated to 1.7 mg/mL (BtIspE) or 2.8 mg/ml (BtIspD), aliquoted into 100 μL tubes, flash frozen in liquid nitrogen and stored at −80° C.

Prior to NMR experiments, BtIspD was exchanged into NMR-compatible buffer (25 mM NaCl, 10 mM K-Phos, 10 mM $MgSO_4$, 0.1 mM TCEP, 0.1 mM $NaN_3$, pH 7.0) using cassette dialysis (Thermo Scientific dialysis cassettes, product #66830). Protein was dispensed as 1 mL aliquots at a final concentration of 45 μM, flash frozen in liquid nitrogen, and stored at −20° C.

Similarly, BtIspE was exchanged into NMR-compatible buffer (25 mM NaCl, 10 mM K-Phos, 10 mM $MgSO_4$, 0.1 mM TCEP, 0.1 mM $NaN_3$, 10% (v/v) $^2H_2O$, pH 7.0) using spin column dialysis (Sartorius Vivaspin Turbo 15 spin columns, product #VS15T01). Protein was dispensed as 1 mL aliquots at a final concentration of 80 μM, flash frozen in liquid nitrogen, and stored at −20° C.

NMR Spectroscopy

BtIspD: NMR samples were prepared by diluting concentrated protein, described above, to 20 μM in NMR-compatible buffer (25 mM NaCl, 10 mM K-Phos, 10 mM $MgSO_4$, 0.1 mM TCEP, 0.1 mM sodium azide, 5% (v/v) $^2H_2O$, final pH=7.0). Compounds were assayed at ligand concentrations of 250 μM, with 25 μL deuterated dimethyl sulfoxide ($d_6$-DMSO) present in a 500 μL sample volume. All experiments were conducted on a Varian Inova 500 MHz NMR spectrometer equipped with a standard HCN probe at a temperature of 10° C. Screening was completed using ligand-observe proton-based one-dimensional saturation transfer difference nuclear magnetic resonance (STD-NMR).[4] Briefly, 64 scans and 16,384 points were acquired over a 16 ppm sweep width, with a total recycle delay of 4.0 s for each mixture. A low-power 30 ms spin-lock pulse was added to filter our low-level protein peaks, and a DPFGSE sequence was used to suppress the bulk water signal. STD-NMR pre-saturation was completed using a 3.0 s long train of Gaussian-shaped pulses with a spectral width of 500 Hz focused at 0 ppm, with reference irradiation set to 30 ppm. NMR spectra were processed and analyzed using MestReNova (Mestrelab). If significant protein-ligand interactions were observed in the initial sample, the sample was spiked with 500 μM CDP and a second data set was acquired.

BtIspE: NMR samples were prepared by diluting concentrated IspE protein, described above, to 30 μM with NMR-compatible buffer (25 mM NaCl, 10 mM K-Phos, 10 mM $MgSO_4$, 0.1 mM TCEP, 0.1 mM sodium azide, 10% (v/v) $^2H_2O$, final pH=7.0). Compounds were assayed at ligand concentrations of 250 μM, with 25 μL deuterated dimethyl sulfoxide ($d_6$-DMSO) present in a 500 μL sample volume. STD-NMR experiments were performed and analyzed using conditions identical to those for IspD, above. If significant protein-ligand interactions were observed in the initial sample, the sample was first spiked with 500 μM ADP before acquisition of a second data set, then spiked with 500 μM CDP before acquisition of a third data set.

Example 1—Synthesis of 4,6-dichloropyrimidine-5-carbaldehyde 1

This compound was synthesized similar to a patent.[5] To $POCl_3$ (107.3 mmol, 10 mL) cooled at 0° C. was added DMF (41.3 mmol, 3.2 mL) dropwise, and the mixture was stirred for 1 h. Then, 4,6-dihydroxylpyrimidine (22.3 mmol, 2.50 g) was added, stirred for 30 minutes and refluxed for 3 h. After removing the volatiles at reduced pressure, it was poured into ice and extracted with ethyl acetate three times (3×200 mL). The combined ethyl acetate extracts were washed with 200 mL saturated $NaHCO_3$, dried with $Na_2SO_4$, and concentrated under reduced pressure to afford 2.91 g, 74% of the desired compound as an orange solid. $^1H$ NMR (500 MHz, $CDCl_3$): δ 10.48 (s, 1H), 9.92 (s, 1H). $^{13}C$ NMR (125 MHz, $CDCl_3$): δ 185.61, 162.69, 159.58, 124.89.

Example 2—Synthesis of 4-chloro-1-methyl-1H-pyrazolo[3,4-d]pyrimidine 2

To 4,6-dichloro-pyrimidine-5-carbaldehyde (2.90 g, 16.39 g) and diisopropylethylamine (2.12 g, 2.85 mL, 16.39 mmol) in THF (100 mL) cooled at 0° C. was added dropwise methylhydrazine (0.83 g, 0.95 mL, 18.03 mmol) in 10 mL THF. The reaction mixture was stirred at 0° C. for 10 min, and warmed to room temperature and stirred for 3 h. Then, the solvent was removed at reduced pressure and the crude was chromatographed by Biotage (DCM: EtOAc) to afford 1.47 g, 53% of the desired compound as a white solid. $^1H$ NMR (300 MHz, $CDCl_3$): δ 8.79 (s, 1H), 8.17 (s, 1H), 4.17 (s, 3H). $^{13}C$ NMR (75 MHz, $CDCl_3$): δ 154.83, 154.53, 153.23, 131.90, 113.65, 34.47.

Example 3—General Procedure for the Synthesis of Pyrazolopyrimidine Derivatives A mixture of 4-chloro-1-methyl-1H-pyrazolo[3,4-d]pyrimidine (165.58 mg, 1.0 mmol), the corresponding primary amine (1.0 mmol), and diisopropylamine (129.24 mg, 1.0 mmol) in 10 ml THF was heated at 60° C. overnight under nitrogen atmosphere. The reaction mixture was partitioned between ethyl acetate (30 mL) and water (30 mL). The aqueous layer was extracted with ethyl acetate (2×30 ml). The combined organic layers were dried with anhydrous $Na_2SO_4$ and the solvent was removed at reduced pressure to afford the corresponding pyrazolopyrimidine derivative. Some of the compounds had impurities and passed through a column (DCM: EtOAc), but most of the compounds were pure and used without further purification.

Example 4—Synthesis of Compound 3

3

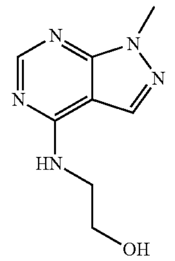

Compound 3 was partially soluble in water and ethyl acetate. The ethyl acetate extract was dried with anhydrous $Na_2SO_4$ and the solvent was removed under reduced pressure. Then, water was lyophilized and the combined crude was chromatographed using Biotage (DCM: MeOH) to afford compound 3 as a white solid (187 mg, 62%). mp 196-198° C. FT-IR: ν=3250.52, 3139.86, 3036.77, 2960.85, 2944.15, 2869.27, 1612.11, 1569.82, 1539.92, 1494.92, 1458.02, 1426.80, 1381.16, 1314.46, 1270.97, 1189.30, 1125.07, 1052.51, 1003.04, 920.63, 874.68, 786.77, 743.30, 644.80 $cm^{-1}$. $^1H$ NMR (500 MHz, DMSO-$d_6$): δ 8.31 (br s, 1H), 8.24 (s, 1H), 8.12 (s, 1H), 4.85 (br s, 1H), 3.88 (s, 3H), 3.57-3.55 (m, 4H). $^{13}C$ NMR (75 MHz, DMSO-$d_6$): δ 156.94, 156.05, 153.02, 131.95, 100.82, 60.01, 43.29, 33.86. Analytical HPLC (Ret time; 1.68 min, Height (mAU); 1675.50, Area %; 92.3%). HRMS (ESI-TOF) m/z: $[M+H]^+$ Calcd for $C_8H_{12}N_5O$ 194.1042; Found 194.1043.

Example 5—Synthesis of Compound 4

4

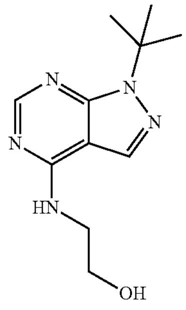

The crude was purified by Biotage (MeOH:DCM) to afford compound 4 as a pale orange solid (91.5 mg, 39%). mp 75-77° C. FT-IR: ν=3295.29, 3179.70, 2989.23, 2946.60, 2869.53, 1620.12, 1558.43, 1533.58, 1461.37, 1383.09, 1298.83, 1236.85, 1170.48, 1060.94, 994.46, 927.11, 869.88, 787.93, 662.56, 629.16 $cm^{-1}$. $^1H$ NMR (300 MHz, DMSO-$d_6$): δ 8.21 (br s, 2H), 8.08 (s, 1H), 4.82-4.81 (m, 1H), 3.59-3.54 (m, 4H), 1.69 (s, 9H). $^{13}C$ NMR (75 MHz, DMSO-$d_6$): δ 157.11, 154.89, 152.74, 130.22, 102.33, 60.05, 59.72, 43.14, 29.24. Analytical HPLC (Ret time; 1.93 min, Height (mAU); 2212.91, Area %; 99.3%). HRMS (ESI-TOF) m/z: $[M+H]^+$ Calcd for $C_{11}H_{18}N_5O$ 236.1511; Found 236.1512.

Example 6—Synthesis of Compound 5

5

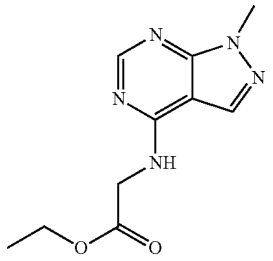

The crude was purified by Biotage (MeOH:DCM) to afford compound 5 a white solid (136 mg, 58%). mp 141-142° C. FT-IR: ν=3356.65, 3134.73, 2975.53, 2931.59, 1717.29, 1610.77, 1569.11, 1533.31, 1499.77, 1405.50, 1375.53, 1341.95, 1306.86, 1272.91, 1230.08, 1137.17, 1015.03, 979.94, 902.66, 852.48, 790.52, 731.44, 646.60 $cm^{-1}$. $^1H$ NMR (300 MHz, DMSO-$d_6$): δ 7.47 (s, 1H), 7.27 (s, 1H), 4.08 (s, 3H), 3.53 (s, 2H), 3.41 (q, J=6.9 Hz, 2H), 0.47 (t, J=6.9 Hz, 3H). $^{13}C$ NMR (75 MHz, DMSO-$d_6$): δ 169.55, 156.26, 154.42, 151.50, 130.21, 100.03, 60.11, 40.90, 31.86, 12.23. Analytical HPLC (Ret time; 1.98 min, Height (mAU); 1912.63, Area %; 92.4%). HRMS (ESI-TOF) m/z: $[M+H]^+$ Calcd for $C_{10}H_{14}N_5O_2$ 236.1147; Found 236.1150.

Example 7—Synthesis of Compound 6

6

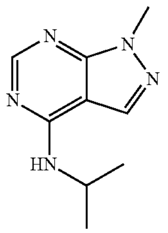

The crude was purified by Biotage (EtOAc:DCM) to afford compound 6 as an off-white solid (118 mg, 62%). mp 101-103° C. FT-IR: ν=3241.86, 3177.60, 3125.00, 3026.78, 2968.42, 6003.86, 1567.24, 1536.22, 1484.73, 1446.90, 1381.39, 1319.56, 1265.85, 1163.12, 1127.92, 1055.54, 986.96, 946.88, 906.36, 786.90, 741.42, 637.88 $cm^{-1}$. $^1H$ NMR (300 MHz, DMSO-$d_6$): δ 8.23 (br s, 1H), 8.10 (s, 1H), 8.04-8.00 (m, 1H), 4.40 (sep, J=6.6 Hz, 1H), 3.87 (s, 3H), 1.22 (d, J=6.6 Hz, 6H). $^{13}C$ NMR (75 MHz, DMSO-$d_6$): δ 155.62, 155.49, 152.59, 131.28, 100.17, 41.53, 33.33, 22.29. Analytical HPLC (Ret time; 2.53 min, Height (mAU); 1940.66, Area %; 98.7%). HRMS (ESI-TOF) m/z: $[M+H]^+$ Calcd for $C_9H_{14}N_5$ 192.1249; Found 192.1254.

Example 8—Synthesis of Compound 7

7

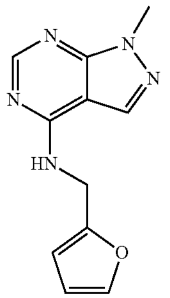

Compound 7 was obtained as a tan solid (224 mg, 98%). mp 141-143° C. FT-IR: ν=3249.30, 3146.07, 3104.44, 3030.75, 2951.95, 2884.86, 2706.50, 1666.73, 1608.83, 1565.23, 1542.01, 1497.28, 1425.38, 1383.38, 1323.29, 1265.02, 1229.33, 1989.11, 1145.43, 1095.03, 1073.87, 1005.32, 983.59, 917.96, 897.57, 788.40, 740.14, 647.59, 620.59 $cm^{-1}$. $^1H$ NMR (300 MHz, DMSO-$d_6$): δ 8.75 (br s, 1H), 8.35 (s, 1H), 8.18 (s, 1H), 7.66-7.65 (m, 1H), 6.47-6.46 (m, 1H), 6.40-6.39 (m, 1H), 4.79 (d, J=5.7 Hz, 2H), 3.95 (s, 3H). $^{13}C$ NMR (75 MHz, DMSO-$d_6$): δ 155.98, 155.47, 152.61, 151.93, 142.28, 131.32, 110.48, 107.37, 100.27, 36.47, 33.40. Analytical HPLC (Ret time; 2.44 min, Height (mAU); 1800.65, Area %; 94.1%). HRMS (ESI-TOF) m/z: $[M+H]^+$ Calcd for $C_{11}H_{12}N_5O$ 230.1042; Found 230.1045.

Example 9—Synthesis of Compound 8

8

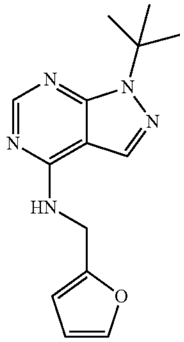

The crude was purified by Biotage (EtOAc:DCM) to afford compound 8 as an off-white solid (200 mg, 74%). mp 101-103° C. FT-IR: ν=3200.79, 3128.29, 3103.89, 3069.40, 2968.48, 2924.44, 2867.31, 1580.53, 1519.57, 1452.93, 1418.04, 1367.62, 1341.27, 1317.33, 1241.94, 1198.77, 1148.38, 1038.49, 1003.05, 919.41, 820.87, 793.01, 764.11, 705.18, 675.48, 639.75 $cm^{-1}$. $^1H$ NMR (300 MHz, DMSO-$d_6$): δ 8.62 (br s, 1H), 8.27 (s, 1H), 8.10 (s, 1H), 7.60-7.59 (m, 1H), 6.41-6.33 (m, 2H), 4.72 (d, J=5.6 Hz, 2H), 1.70 (s, 9H). $^{13}C$ NMR (75 MHz, DMSO-$d_6$): δ 156.63, 154.82, 152.82, 152.55, 142.71, 130.22, 110.97, 107.78, 102.27, 59.81, 36.89, 29.24. Analytical HPLC (Ret time; 3.61 min, Height (mAU); 927.71, Area %; 100.0%). HRMS (ESI-TOF) m/z: $[M+H]^+$ Calcd for $C_{14}H_{18}N_5O$ 272.1511; Found 272.1509.

Example 10—Synthesis of Compound 9

9

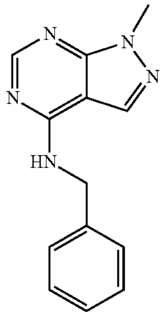

Compound 9 was obtained as an off-white solid (346 mg, 94%). mp 150-152° C. FT-IR: ν=3249.77, 3193.17, 3127.42, 3033.78, 2938.52, 1607.41, 1561.35, 1539.50, 1496.30, 1455.00, 1422.32, 1384.42, 1322.07, 1264.03, 1202.54, 1098.06, 1014.48, 898.85, 862.56, 787.39, 747.00, 701.10, 635.45 $cm^{-1}$. $^1H$ NMR (300 MHz, DMSO-$d_6$): δ 8.75 (t, J=5.4 Hz, 1H), 8.27 (s, 1H), 8.14 (s, 1H), 7.38-7.23 (m, 5H), 4.75 (d, J=6.0 Hz, 2H), 3.90 (s, 3H). $^{13}C$ NMR (75 MHz, DMSO-$d_6$): δ 156.78, 156.11, 153.14, 139.70, 131.77, 128.84, 127.87, 127.39, 100.75, 43.64, 33.90. Analytical HPLC (Ret time; 4.14 min, Height (mAU); 1072.02, Area %; 100.0%). HRMS (ESI-TOF) m/z: $[M+H]^+$ Calcd for $C_{13}H_{14}N_5$ 240.1249; Found 240.1248.

Example 11—Synthesis of Compound 10

10

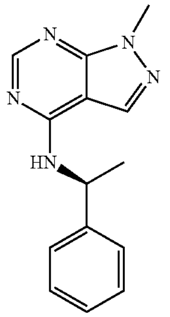

Compound 10 was obtained as a pale yellow solid (222 mg, 88%). mp 201-203° C. FT-IR: ν=3235.07, 3156.20, 3100.40, 3027.40, 2970.92, 2934.11, 2360.42, 1669.15, 1607.42, 1570.72, 1536.41, 1494.61, 1448.80, 1385.14, 1325.67, 1271.80, 1197.51, 1189.94, 1113.45, 1068.04, 1034.44, 986.24, 924.33, 890.83, 816.87, 789.59, 737.28, 694.61, 646.36 $cm^{-1}$. $^1H$ NMR (300 MHz, DMSO-$d_6$): δ 8.59 (d, J=7.8 Hz, 1H), 8.20 (s, 2H), 7.42-7.19 (m, 5H), 5.52 (quin, J=7.2 Hz, 1H), 3.88 (s, 3H), 1.53 (d, J=6.9 Hz, 3H). $^{13}C$ NMR (75 MHz, DMSO-$d_6$): δ 156.01, 153.14, 145.02, 131.90, 128.85, 128.78, 127.16, 126.70, 100.71, 49.27, 33.86, 22.92. Analytical HPLC (Ret time; 3.25 min, Height (mAU); 1499.91, Area %; 100.0%). HRMS (ESI-TOF) m/z: $[M+H]^+$ Calcd for $C_{14}H_{16}N_5$ 254.1406; Found 254.1407.

Example 12—Synthesis of Compound 11

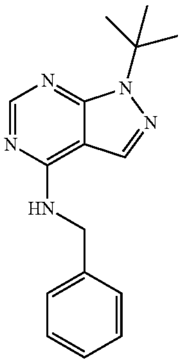

11

The crude was chromatographed by Biotage (EtOAc:hexane) to afford compound 11 as a pale yellow solid (210 mg, 75%). mp 158-160° C. FT-IR: ν=3207.64, 3069.88, 2973.83, 2928.56, 2864.25, 1590.21, 1451.15, 1345.16, 1317.18, 1232.99, 1091.55, 1030.63, 1001.94, 975.77, 917.23, 868.44, 791.18, 751.64, 697.55 $cm^{-1}$. $^1H$ NMR (300 MHz, DMSO-$d_6$): δ 8.69 (t, J=5.7 Hz, 1H), 8.24 (s, 1H), 8.11 (s, 1H), 7.37-7.22 (m, 5H), 4.73 (d, J=6.0 Hz, 2H), 1.70 (s, 9H). $^{13}C$ NMR (75 MHz, DMSO-$d_6$): δ 156.89, 154.96, 152.80, 139.82, 130.16, 128.82, 127.85, 127.35, 102.23, 59.79, 43.52, 29.25. Analytical HPLC (Ret time; 6.02 min, Height (mAU); 803.13, Area %; 100.0%). HRMS (ESI-TOF) m/z: $[M+H]^+$ Calcd for $C_{16}H_{20}N_5$ 282.1719; Found 282.1723.

Example 13—Synthesis of 4-chloro-1-phenyl-1H-pyrazolo[3,4-d]pyrimidine

To 4,6-dichloro-pyrimidine-5-carbaldehyde (2.13 g, 12 mmol) and diisopropylethylamine (1.55 g, 2.1 mL, 12 mmol) in THF (50 mL) cooled at 0° C. was added dropwise phenylhydrazine (1.37 g, 1.1 mL, 13.2 mmol) in 15 mL THF. The reaction mixture was stirred at 0° C. for 20 min, and warmed to room temperature and stirred for overnight. The solvent was removed at reduced pressure and the crude was chromatographed by Biotage (EtOAc:hexane) to give 0.635 g. However, proton nmr of the compound did not show the formation of pyrazolo-pyrimidine ring. Therefore similar to the reported procedure,[6] 357 mg of the hydrazone was heated in a microwave at 200° C. in the presence of 3 mL acetonitrile. The crude was chromatographed by Biotage (EtOAc:hexane) to afford 247 mg, 80% of the desired compound. $^1H$ NMR (300 MHz, DMSO-$d_6$): δ 8.99 (s, 1H), 8.77 (s, 1H), 8.17-8.14 (m, 2H), 7.65-7.59 9 (m, 2H), 7.48-7.42 (m, 1H). $^{13}C$ NMR (75 MHz, DMSO-$d_6$): δ 155.90, 154.64, 153.08, 138.28, 134.52, 129.92, 127.88, 121.83, 115.15.

Example 14—Synthesis of Compound 12

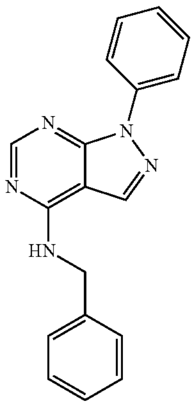

12

A mixture of 4-chloro-1-phenyl-1H-pyrazolo[3,4-d]pyridine (213 mg, 0.92 mmol), benzylamine (118 mg, 0.12 mL, 1.1 mmol) and diisopropylamine (142 mg, 0.19 mL, 1.1 mmol) in 15 mL of THF was heated at 60° C. overnight under nitrogen atmosphere. After removing the solvent using rotavapor, the crude was partitioned between ethyl acetate (30 mL) and water (30 mL). The aqueous layer was extracted with ethyl acetate two times (2×30 mL). The combined organic layers were dried with anhydrous $Na_2SO_4$ and the solvent was removed under reduced pressure. The crude was chromatographed using Biotage (EtOAc:hexane) to afford compound 12 as a white solid (204 mg, 74%). mp 184-186° C. FT-IR: ν=3202.91, 3081.52, 2922.86, 2865.32, 2217.52, 1594.90, 1580.47, 1537.45, 1498.24, 1465.96, 1420.63, 1304.29, 1235.05, 1102.26, 1083.18, 1062.63, 1029.26, 964.80, 919.89, 864.34, 788.34, 750.25, 699.83, 628.66 $cm^{-1}$. $^1H$ NMR (300 MHz, DMSO-$d_6$): δ 8.97 (t, J=5.7 Hz, 1H), 8.44 (s, 1H), 8.39 (s, 1H), 8.20 (d, J=7.8 Hz, 2H), 7.57-7.52 (m, 2H), 7.41-7.24 (m, 6H), 4.79 (d, J=6.0 Hz, 2H). $^{13}C$ NMR (75 MHz, DMSO-$d_6$): δ 157.00, 156.96, 153.34, 139.47, 139.37, 134.19, 129.61, 128.90, 127.95, 127.49, 126.62, 121.12, 102.26, 43.73. Analytical HPLC (Ret time; 10.92 min, Height (mAU); 1177.67, Area %; 94.8%). HRMS (ESI-TOF) m/z: $[M+H]^+$ Calcd for $C_{18}H_{16}N_5$ 302.1406; Found 302.1407.

Example 15—Synthesis of Compound 13

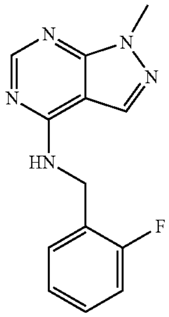

13

Compound 13 was obtained as a pale yellow solid (250 mg, 97%). mp 184-185° C. FT-IR: ν=3241.40, 3180.73, 3127.50, 3035.54, 2937.50, 2875.38, 1610.77, 1570.83, 1539.15, 1496.60, 1458.31, 1431.17, 1386.60, 1334.28, 1317.67, 1271.55, 1231.26, 1104.45, 987.13, 911.78, 867.94, 790.40, 753.91, 642.73 $cm^{-1}$. $^{1}H$ NMR (300 MHz, DMSO-$d_6$): δ 8.74 (br s, 1H), 8.27 (s, 1H), 8.15 (s, 1H), 7.42-7.12 (m, 4H), 4.78 (d, J=6.0 Hz, 2H), 3.90 (s, 3H). $^{13}C$ NMR (75 MHz, DMSO-$d_6$): δ 162.35, 159.11, 156.70, 156.03, 153.10, 131.80, 130.22, 130.16, 129.60, 129.49, 126.34, 126.14, 124.87, 124.83, 115.52, 100.78, 37.67, 33.91. Analytical HPLC (Ret time; 2.49 min, Height (mAU); 2163.71, Area %; 100.0%). HRMS (ESI-TOF) m/z: $[M+H]^+$ Calcd for $C_{13}H_{13}N_5F$ 258.1155; Found 258.1156.

Example 16—Synthesis of Compound 14

14

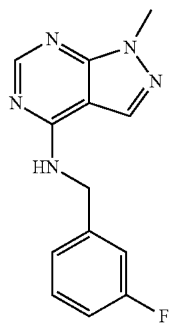

Compound 14 was obtained as pale yellow solid (266 mg, 98%). mp 176-177° C. FT-IR: ν=3243.49, 3197.79, 3130.58, 3033.65, 2937.50, 2873.83, 1610.13, 1572.60, 1537.67, 1493.66, 1386.56, 1334.04, 1318.36, 1272.17, 1254.61, 1201.44, 1141.61, 1107.12, 983.65, 916.50, 868.63, 725.74, 688.61, 644.45 $cm^{-1}$. $^{1}H$ NMR (500 MHz, DMSO-$d_6$): δ 8.78 (br s, 1H), 8.28 (s, 1H), 8.14 (s, 1H), 7.40-7.34 (m, 1H), 7.21-7.16 (m, 2H), 7.10-7.06 (m, 1H), 4.77 (d, J=3.6 Hz, 2H), 3.91 (s, 3H). $^{13}C$ NMR (125 MHz, DMSO-$d_6$): δ 163.69, 161.75, 156.78, 156.06, 153.19, 142.86, 142.81, 131.73, 130.83 130.77 114.55, 114.38, 114.21, 114.05, 100.80, 43.19, 33.92. Analytical HPLC (Ret time; 3.51 min, Height (mAU); 1283.35, Area %; 100.0%). HRMS (ESI-TOF) m/z: $[M+H]^+$ Calcd for $C_{13}H_{13}N_5F$ 258.1155; Found 258.1153.

Example 17—Synthesis of Compound 15

15

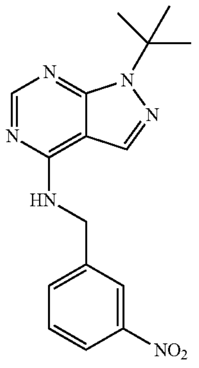

The crude was purified by Biotage (EtOAc:DCM) to afford compound 15 as an orange solid (116 mg, 59%). mp 135-137° C. FT-IR: ν=3404.80, 3258.53, 3200.24, 3120.68, 3030.82, 2971.81, 2937.37, 1604.65, 1558.73, 1520.73, 1483.16, 1447.70, 1354.31, 1309.79, 1282.60, 1169.57, 1107.21, 1060.35, 1019.28, 967.06, 893.71, 790.98, 740.47, 696.34, 672.13, 635.60 $cm^{-1}$. $^{1}H$ NMR (300 MHz, $CD_3OD$): δ 8.23-8.22 (m, 2H), 8.07-7.99 (m, 2H), 7.77-7.75 (m, 1H), 7.54-7.48 (m, 1H), 4.89-4.86 (m, 2H), 1.72 (s, 9H). $^{13}C$ NMR (75 MHz, $CD_3OD$): δ 156.85, 154.10, 152.37, 148.31, 141.44, 133.42, 129.30, 121.85, 121.67, 102.11, 59.86, 42.96, 28.07. Analytical HPLC (Ret time; 5.27 min, Height (mAU); 1088.63, Area %; 97.1%). HRMS (ESI-TOF) m/z: $[M+H]^+$ Calcd for $C_{16}H_{19}N_6O_2$ 327.1569; Found 327.1566.

Example 18—Synthesis of Compound 16

16

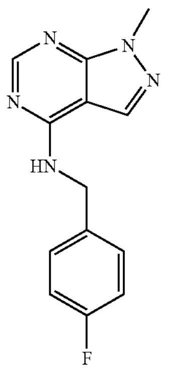

Compound 16 was obtained as pale yellow solid (249 mg, 97%). mp 148-149° C. FT-IR: ν=3240.66, 3172.42, 3116.09, 3037.94, 2906.11, 2873.68, 1882.49, 1761.82, 1605.22, 1567.02, 1535.59, 1511.94, 1432.45, 1383.91, 1316.90, 1264.57, 1215.82, 1154.04, 1098.50, 980.00, 915.50, 827.44, 789.32, 741.95, 724.82, 634.78 $cm^{-1}$. $^{1}H$ NMR (300 MHz, DMSO-$d_6$): δ 8.76 (t, J=5.4 Hz, 1H), 8.27 (s, 1H), 8.12 (s, 1H), 7.42-7.37 (m, 2H), 7.18-7.12 (m, 2H), 4.74 (d, J=6.0 Hz, 2H), 3.90 (s, 3H). $^{13}C$ NMR (75 MHz, DMSO-$d_6$): δ 163.32, 160.11, 156.69, 156.09, 153.12, 135.92, 131.73, 129.90, 129.79, 115.71, 115.43, 100.74, 42.92, 33.91. Analytical HPLC (Ret time; 2.71 min, Height (mAU); 1514.99, Area %; 100.0%). Anal. Calcd for $C_{13}H_{12}FN_5$: C, 60.69; H, 4.70; N, 27.22. Found: C, 60.76; H, 4.41; N, 26.23. HRMS (ESI-TOF) m/z: $[M+H]^+$ Calcd for $C_{13}H_{13}N_5F$ 258.1155; Found 258.1154.

Example 19—Synthesis of FOL7185 (Compound 17)

FOL7185

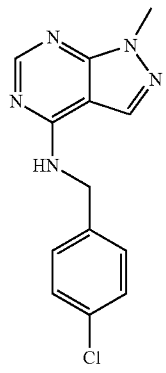

FOL7185 (17) was obtained as an off-white solid (257 mg, 93%). mp 197-199° C. FT-IR: ν=3199.30, 3127.47, 3036.89, 2969.28, 2928.23, 2875.62, 1593.05, 1565.19 1533.75, 1490.40 1315.66, 1251.43, 1090.60, 1015.11, 917.21, 789.10, 742.25, 664.06, 609.67 $cm^{-1}$. $^1H$ NMR (300 MHz, DMSO-$d_6$): δ 8.79 (t, J=5.7 Hz, 1H), 8.26 (s, 1H), 8.12 (s, 1H), 7.44-7.31 (m, 4H), 4.73 (d, J=6.0 Hz, 2H), 3.90 (s, 3H). $^{13}C$ NMR (75 MHz, DMSO-$d_6$): δ 156.70, 156.07, 153.11, 138.83, 131.90, 131.71, 129.66, 128.79, 100.75, 42.94, 33.92. Analytical HPLC (Ret time; 4.04 min, Height (mAU); 677.81, Area %; 97.8%). HRMS (ESI-TOF) m/z: $[M+H]^+$ Calcd for $C_{13}H_{13}N_5Cl$ 274.0859; Found 274.0863.

Example 20—Synthesis Compound 18

18

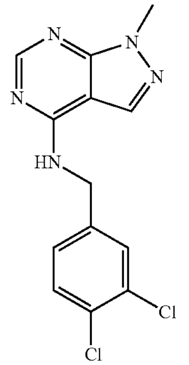

Compound 18 was obtained as a pale yellow solid (243 mg, 79%). mp 170-173° C. FT-IR: ν=3247.28, 3201.93, 3129.08, 3038.52, 2937.93, 2879.22, 1607.69, 1564.54, 1532.20, 1492.00, 1465.99, 1387.96, 1310.31, 1266.96, 1203.21, 1130.15, 1105.49, 1029.98, 982.22, 915.63, 891.00, 820.21, 786.93, 745.07, 687.02, 663.31, 621.95 $cm^{-1}$. $^1H$ NMR (300 MHz, DMSO-$d_6$): δ 8.81 (t, J=5.7 Hz, 1H), 8.27 (s, 1H), 8.12 (s, 1H), 7.60-7.57 (m, 2H), 7.35-7.32 (m, 1H), 4.74 (d, J=5.7 Hz, 2H), 3.90 (s, 3H). $^{13}C$ NMR (75 MHz, DMSO-$d_6$): δ 156.64, 156.03, 153.10, 141.14, 131.69, 131.38, 131.05, 129.86, 129.73, 128.13, 100.77, 42.58, 33.94. Analytical HPLC (Ret time; 5.77 min, Height (mAU); 1068.97, Area %; 100.0%). HRMS (ESI-TOF) m/z: $[M+H]^+$ Calcd for $C_{13}H_{12}N_5Cl_2$ 308.0470; Found 308.0466.

Example 21—Synthesis of Compound of 19

19

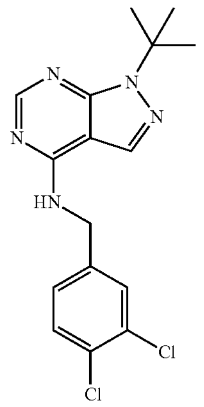

The crude was purified by Biotage (EtOAc:DCM) to afford compound 19 as an off-white solid (139 mg, 66%). mp 120-123° C. FT-IR: ν=3405.67, 3256.56, 3200.07, 3125.09, 3034.69, 2977.04, 1607.47, 1556.57, 1530.35, 1473.45, 1424.20, 1384.99, 1322.55, 1238.92, 1170.93, 1128.90, 1061.13, 1027.64, 985.87, 963.18, 900.52, 861.92, 818.44, 879.49, 718.80, 684.85, 630.25, 608.46 $cm^{-1}$. $^1H$ NMR (300 MHz, $CD_3OD$): δ 8.22 (s, 1H), 7.97 (br s, 1H), 7.47 (d, J=1.8 Hz, 1H), 7.36-7.33 (m, 1H), 7.25-7.21 (m, 1H), 4.71 (s, 2H), 1.71 (s, 9H). $^{13}C$ NMR (75 MHz, $CD_3OD$): δ 156.80, 154.12, 152.37, 139.73, 131.94, 130.52, 130.16, 129.34, 129.16, 126.91, 102.14, 59.84, 42.64, 28.15. Analytical HPLC (Ret time; 9.61 min, Height (mAU); 403.97, Area %; 100.0%). HRMS (ESI-TOF) m/z: $[M+H]^+$ Calcd for $C_{16}H_{18}N_5Cl_2$ 350.0939; Found 350.0940.

Example 22—Synthesis of Compound 20

20

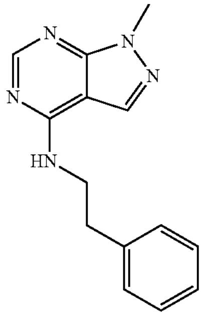

Compound 20 was obtained as a white solid (210 mg, 83%). mp 101-103° C. FT-IR: ν=3231.71, 3081.40, 2941.72, 2876.95, 1535.80, 1506.86, 1410.12, 1328.85, 1264.21, 1213.48, 1106.89, 987.23, 913.03, 785.56, 747.88, 694.22, 628.29 $cm^{-1}$. $^1H$ NMR (300 MHz, DMSO-$d_6$): δ 8.36 (t, J=5.4 Hz, 1H), 8.28 (s, 1H), 8.07 (s, 1H), 7.33-7.17 (m, 5H), 3.88 (s, 3H), 3.75-3.69 (m, 2H), 2.93 (t, J=7.2 Hz, 2H). $^{13}C$ NMR (75 MHz, DMSO-$d_6$): δ 156.74, 156.15, 153.04, 139.88, 131.66, 129.15, 128.82, 126.60, 100.77, 42.01, 35.32, 33.87. Analytical HPLC (Ret time; 3.00 min, Height (mAU); 1123.93, Area %; 100.0%). HRMS (ESI-TOF) m/z: $[M+H]^+$ Calcd for $C_{14}H_{16}N_5$ 254.1406; Found 254.1406.

Example 23—Synthesis of Compound 21

21

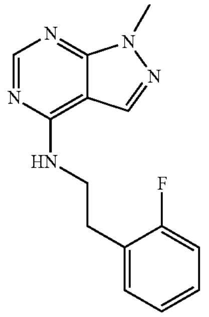

Compound 21 was obtained as a pale yellow solid (236 mg, 87%). mp 139-140° C. FT-IR: ν=3240.36, 3084.48, 2922.50, 1611.08, 1586.43, 1550.03, 1487.34, 1452.19, 1324.17, 1259.88, 1225.64, 1111.49, 984.90, 913.14, 806.97, 756.34, 693.58, 632.06 $cm^{-1}$. $^1H$ NMR (300 MHz, DMSO-$d_6$): δ 8.39 (t, J=5.4 Hz, 1H), 8.27 (s, 1H), 8.05 (s, 1H), 7.33-7.23 (m, 2H), 7.18-7.09 (m, 2H), 3.89 (s, 3H), 3.76-3.70 (m, 2H), 2.97 (t, J=7.2 Hz, 2H). $^{13}C$ NMR (75 MHz, DMSO-$d_6$): δ 162.83, 159.76, 156.74, 156.11, 153.03, 131.72, 131.65, 131.62, 128.86, 128.76, 126.54, 126.33, 124.88, 124.83, 115.74, 115.45, 100.78, 40.63, 33.87, 28.78. Analytical HPLC (Ret time; 8.43 min, Height (mAU); 1580.45, Area %; 100.0%). HRMS (ESI-TOF) m/z: $[M+H]^+$ Calcd for $C_{19}H_{15}N_5F$ 272.1311; Found 272.1315.

Example 24—Synthesis of Compound 22

22

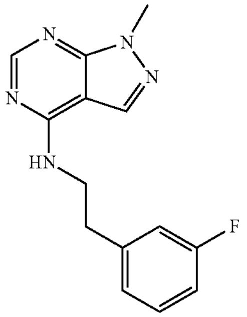

Compound 22 was obtained as a yellow solid (263 mg, 97%). mp 109-110° C. FT-IR: ν=3227.08, 3074.78, 2700.59, 1582.31, 1483.48, 1450.03, 1331.38, 1266.38, 1244.81, 1201.34, 1137.23, 1110.71, 987.34, 913.18, 861.30, 788.06, 751.89, 691.34, 631.12 $cm^{-1}$. $^1H$ NMR (300 MHz, DMSO-$d_6$): δ 8.35 (br s, 1H), 8.28 (s, 1H), 8.07 (s, 1H), 7.36-7.29 (m, 1H), 7.12-6.99 (m, 3H), 3.88 (s, 3H), 3.74 (q, J=6.3 Hz, 2H), 2.95 (t, J=7.2 Hz, 2H). $^{13}C$ NMR (75 MHz, DMSO-$d_6$): δ 164.28, 161.06, 156.73, 156.11, 153.03, 142.91, 142.82, 131.64, 130.67, 130.56, 125.36, 125.33, 115.99, 115.72, 113.52, 113.24, 100.77, 41.59, 34.89, 33.87. Analytical HPLC (Ret time; 3.72 min, Height (mAU); 935.43, Area %; 99%). HRMS (ESI-TOF) m/z: $[M+H]^+$ Calcd for $C_{14}H_{15}N_5F$ 272.1311; Found 272.1315.

Example 25—Synthesis of Compound 23

23

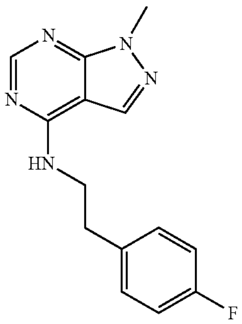

Compound 23 was obtained as a pale yellow solid (249 mg, 97%). mp 106-107° C. FT-IR: ν=3241.69, 3088.25, 2940.64, 1589.26, 1507.80, 1435.50, 1327.74, 1260.53, 1213.76, 1159.34, 1108.24, 983.70, 913.51, 832.84, 785.08, 752.88, 693.77, 608.03 $cm^{-1}$. $^1H$ NMR (300 MHz, DMSO-$d_6$): δ 8.35 (t, J=5.4 Hz, 1H), 8.27 (s, 1H), 8.07 (s, 1H), 7.31-7.26 (m, 2H), 7.15-7.07 (m, 2H), 3.88 (s, 3H), 3.74-3.67 (m, 2H), 2.91 (t, J=7.5 Hz, 2H). $^{13}C$ NMR (75 MHz, DMSO-$d_6$): δ 162.91, 159.71, 156.74, 156.12, 153.02, 136.04, 136.00, 131.66, 130.99, 130.89, 115.61, 115.33, 100.76, 41.99, 34.40, 33.87. Analytical HPLC (Ret time; 3.58 min, Height (mAU); 708.07, Area %; 100.0%). HRMS (ESI-TOF) m/z: $[M+H]^+$ Calcd for $C_{14}H_{15}N_5F$ 272.1311; Found 272.1313.

Example 26—Synthesis of Compound 24

24

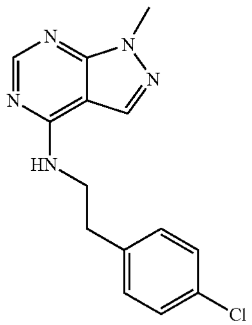

Compound 24 was obtained as a white solid (260 mg, 90%). mp 152-153° C. FT-IR: ν=3212.60, 3011.65, 2941.94, 2868.48, 1579.96, 1491.82, 1437.07, 1342.64, 1320.69, 1265.37, 1073.82, 1019.88, 992.15, 912.47, 868.60, 836.99, 806.24, 787.83, 751.03, 713.79, 661.92, 629.44 $cm^{-1}$. $^1H$ NMR (300 MHz, DMSO-$d_6$): δ 8.33 (br s, 1H), 8.27 (s, 1H), 8.06 (s, 1H), 7.36-7.26 (m, 4H), 3.88 (s, 3H), 3.74-3.68 (m, 2H), 2.92 (t, J=7.2 Hz, 2H). $^{13}C$ NMR (75 MHz, DMSO-$d_6$): δ 156.73, 156.11, 153.03, 138.93, 131.64, 131.25, 131.07, 128.71, 100.76, 41.76, 34.53, 33.87. Analytical HPLC (Ret time; 4.90 min, Height (mAU); 678.91, Area %; 100%). HRMS (ESI-TOF) m/z: $[M+H]^+$ Calcd for $C_{14}H_{15}N_5Cl$ 288.1016; Found 288.1017.

Example 27—Synthesis of Compound 25

25

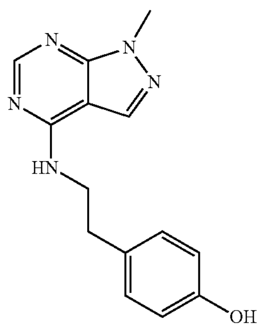

The crude containing compound 25 was purified by Biotage (DCM: EtOAc) to afford 165 mg, 61%) of the compound as pale yellow solid. mp 182-184° C. FT-IR: ν=3375.07, 3228.47, 3097.92, 3015.53, 2939.01, 1600.39, 1566.01, 1510.77, 1447.09, 1330.09, 1260.86, 1235.94, 1106.97, 986.64, 911.55, 831.28, 783.39, 743.24, 699.65, 638.17 $cm^{-1}$. $^1H$ NMR (300 MHz, DMSO-$d_6$): δ 9.19 (s, 1H), 8.32 (t, J=5.1 Hz, 1H), 8.27 (s, 1H), 8.07 (s, 1H), 7.04 (d, J=8.4 Hz, 2H), 6.69-6.66 (m, 2H), 3.88 (s, 3H), 3.68-3.61 (m, 2H), 2.80 (t, J=7.2 Hz, 2H). $^{13}C$ NMR (75 MHz, DMSO-$d_6$): δ 156.72, 156.14, 153.03, 132.34, 130.00, 129.86, 115.59, 100.76, 42.37, 34.53, 33.86. Analytical HPLC (Ret time; 2.04 min, Height (mAU); 1825.44, Area %; 97.0%). HRMS (ESI-TOF) m/z: $[M+H]^+$ Calcd for $C_{14}H_{16}N_5O$ 270.1355; Found 270.1359.

Example 28—Synthesis of Compound 26

26

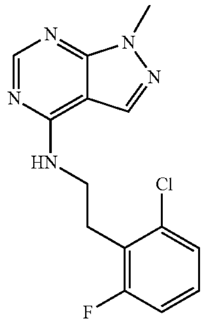

Compound 26 was obtained as a brown solid (216 mg, 71%). mp 195-196° C. FT-IR: ν=3236.02, 3095.44, 2945.29, 1669.45, 1602.74, 1522.12, 1464.30, 1445.89, 1327.11, 1260.61, 1240.89, 1195.06, 1147.85, 1113.99, 1024.34, 985.84, 911.96, 870.03, 773.84, 747.95, 690.30 $cm^{-1}$. $^1H$ NMR (300 MHz, DMSO-$d_6$): δ 8.43 (t, J=5.7 Hz, 1H), 8.24 (s, 1H), 8.03 (s, 1H), 7.32-7.28 (m, 2H), 7.21-7.14 (m, 1H), 3.89 (s, 3H), 3.75-3.68 (m, 2H), 3.12-3.07 (m, 2H). $^{13}C$ NMR (75 MHz, DMSO-$d_6$): δ 162.88, 159.62, 156.34, 155.53, 152.52, 134.52, 134.44, 131.11, 129.07, 128.94, 125.32, 125.28, 124.94, 124.66, 114.42, 114.11, 100.32, 39.20, 33.37, 26.23. Analytical HPLC (Ret time; 4.98 min, Height (mAU); 1197.12, Area %; 98%). HRMS (ESI-TOF) m/z: $[M+H]^+$ Calcd for $C_{14}H_{14}N_5FCl$ 306.0922; Found 306.0926.

Example 29—Synthesis of Compound 27

27

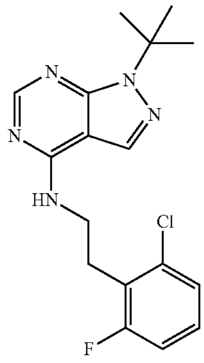

The crude was purified by Biotage (EtOAc:DCM) to afford compound 27 as an off-white solid (197 mg, 42%). mp 140-142° C. FT-IR: ν=3233.90, 3088.91, 2976.44, 2935.93, 1584.79, 1450.37, 1351.41, 1318.06, 1234.86, 1172.77, 1140.27, 1089.55, 1039.37, 1017.15, 983.02, 912.00, 870.83, 824.36, 779.55, 723.19, 662.94, 620.18 $cm^{-1}$. $^1H$ NMR (300 MHz, DMSO-$d_6$): δ 8.35 (br s, 1H), 8.23 (s, 1H), 8.02 (s, 1H), 7.31-7.25 (m, 2H), 7.20-7.14 (m, 1H), 3.73-3.66 (m, 2H), 3.09 (t, J=6.3 Hz, 2H), 1.69 (s, 9H). $^{13}C$ NMR (75 MHz, DMSO-$d_6$): δ 163.36, 160.10, 156.99, 154.90, 152.75, 135.01, 134.93, 130.04, 129.51, 129.38, 125.80, 125.76, 125.42, 125.17, 114.90, 114.59, 102.34, 59.72, 39.03, 29.23, 26.80. Analytical HPLC (Ret time; 6.69 min, Height (mAU); 432.58, Area %; 100.0%). HRMS (ESI-TOF) m/z: $[M+H]^+$ Calcd for $C_{17}H_{20}N_5FCl$ 348.1391; Found 348.1392.

Example 30—Synthesis of Compound 28

28

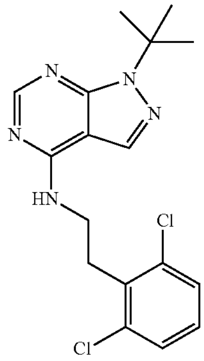

The crude was purified by Biotage (EtOAc:DCM) to afford compound 28 as a white solid (208 mg, 60%). mp 154-156° C. FT-IR: ν=3306.90, 3219.67, 3139.95, 3068.82, 3031.18, 2961.46, 2935.31, 1734.30, 1684.01, 1610.53, 1563.14, 1532.69, 1481.18, 1404.99, 1376.87, 1350.61, 1305.65, 1246.11, 1186.95, 1114.18, 1071.71, 999.38, 973.96, 901.01, 843.45, 791.55, 770.73, 728.44, 648.23 $cm^{-1}$. $^{1}H$ NMR (300 MHz, DMSO-$d_6$): δ 8.36 (t, J=5.1 Hz, 1H), 8.23 (s, 1H), 8.02 (s, 1H), 7.47-7.44 (m, 2H), 7.31-7.25 (m, 1H), 3.75-3.68 (m, 2H), 3.23 (t, J=7.8 Hz, 2H), 1.69 (s, 9H). $^{13}C$ NMR (75 MHz, DMSO-$d_6$): δ 157.03, 154.92, 152.76, 135.47, 135.25, 130.08, 129.57, 128.95, 102.37, 59.74, 38.57, 31.44, 29.25. Analytical HPLC (Ret time; 7.82 min, Height (mAU); 417.11, Area %; 100%). HRMS (ESI-TOF) m/z: $[M+H]^+$ Calcd for $C_{17}H_{20}N_5Cl_2$ 364.1096; Found 364.1091.

Example 31—Synthesis of Compound 29

29

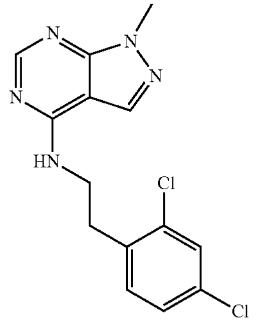

The crude was purified by Biotage to afford compound 29 as a tan solid (444 mg, 90%). mp 145-147° C. FT-IR: ν=3283.54, 3215.19, 3145.03, 3062.28, 3037.70, 2980.35, 2936.49, 1611.67, 1568.91, 1543.25, 1493.74, 1473.36, 1426.29, 1383.13, 1352.74, 1310.00, 1276.08, 1196.65, 1100.49, 1050.49, 987.56, 904.41, 841.37, 788.83, 745.81, 673.97, 664.60 $cm^{-1}$. $^{1}H$ NMR (300 MHz, DMSO-$d_6$): δ 8.35 (t, J=5.1 Hz, 1H), 8.26 (s, 1H), 8.04 (s, 1H), 7.57 (s, 1H), 7.34 (d, J=0.9 Hz, 2H), 3.88 (s, 3H), 3.77-3.70 (m, 2H), 3.03 (t, J=6.9 Hz, 2H). $^{13}C$ NMR (75 MHz, DMSO-$d_6$): δ 156.76, 156.06, 153.02, 136.64, 134.59, 132.86, 132.22, 131.62, 129.08, 127.82, 100.79, 39.90, 33.87, 32.52. Analytical HPLC (Ret time; 7.19 min, Height (mAU); 576.62, Area %; 100.0%). HRMS (ESI-TOF) m/z: $[M+H]^+$ Calcd for $C_{14}H_{14}N_5Cl_2$ 322.0626; Found 322.0624.

Example 32—Synthesis of Compound 30

30

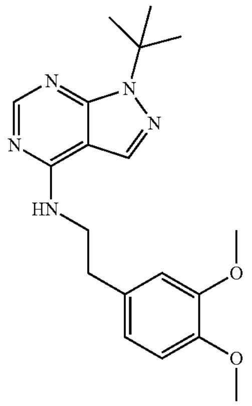

The crude was purified by Biotage (EtOAc:DCM) to afford compound 30 as an off-white solid (210 mg, 98%). mp 79-81° C. FT-IR: ν=3252.97, 3200.97, 3134.77, 3030.81, 2995.00, 2965.08, 2836.88, 2361.21, 2337.81, 1610.96, 1561.38, 1514.92, 1454.86, 1419.13, 1391.68, 1328.88, 1257.73, 1234.68, 1193.58, 1152.92, 1135.21, 1067.61, 1020.01, 975.97, 936.08, 906.02, 867.18, 847.32, 810.47, 788.87, 763.51, 646.78, 624.69 $cm^{-1}$. $^{1}H$ NMR (300 MHz, DMSO-$d_6$): δ 8.25 (br s, 2H), 8.05 (s, 1H), 6.87-6.74 (m, 3H), 3.71 (br s, 8H), 2.85 (t, J=7.2 Hz, 2H), 1.69 (s, 9H). $^{13}C$ NMR (75 MHz, DMSO-$d_6$): δ 156.90, 155.01, 152.74, 149.07, 147.72, 132.37, 130.08, 120.97, 113.07, 112.38, 102.29, 59.74, 55.96, 55.80, 42.02, 34.89, 29.25. Analytical HPLC (Ret time; 5.13 min, Height (mAU); 894.20, Area %; 100.0%). HRMS (ESI-TOF) m/z: $[M+H]^+$ Calcd for $C_{19}H_{26}N_5O_2$ 356.2087; Found 356.2083.

Example 33—Synthesis of Compound 31

31

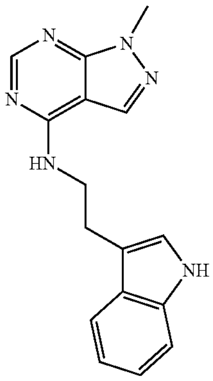

The crude was purified by Biotage to afford 130 mg, 45% of compound 31 as a tan solid. mp 183-185° C. FT-IR: ν=3262.30, 3216.23, 3153.61, 3095.67, 3014.83, 2930.57, 2866.33, 1688.22, 1584.19, 1488.75, 1441.89, 1342.67, 1318.62, 1268.56, 1221.05, 1099.52, 997.82, 913.74, 793.43, 741.04, 709.64, 667.18 $cm^{-1}$. $^{1}H$ NMR (300 MHz, DMSO-$d_6$): δ 10.83 (s, 1H), 8.39 (t, J=5.4 Hz, 1H), 8.30 (s, 1H), 8.07 (s, 1H), 7.58 (d, J=7.8 Hz, 1H), 7.35-7.32 (m, 1H), 7.18 (d, J=2.1 Hz, 1H), 7.09-6.98 (m, 2H), 3.89 (s, 3H), 3.81-3.75 (m, 2H), 3.03 (t, J=7.2 Hz, 2H). $^{13}C$ NMR (75 MHz, DMSO-$d_6$): δ 156.78, 156.21, 153.07, 148.32, 136.70, 131.69, 127.70, 123.20, 121.40, 118.74, 112.20, 111.85, 100.81, 41.31, 33.88, 25.39. Analytical HPLC (Ret time; 3.70 min, Height (mAU); 926.65, Area %; 98%). HRMS (ESI-TOF) m/z: $[M+H]^+$ Calcd for $C_{16}H_{17}N_6$ 293.1515; Found 293.1519.

Kinase-Glo® Enzymatic Assay of Pyrazolopyrimidines for IspE

The Ec IspE gene in parent vector pET14b and the Bt IspE gene in the parent vector AVA0421 were obtained. The vectors were transformed into BL21(DE3) competent cells. Both DNA sequences were verified through University of Chicago CRC-DNA sequencing facility. The sequences are shown in Table 3. The transformed cells were grown on LB agar plates with 100 μg/ml of amp for selection of the expression plasmid, and a single colony was chosen to inoculate a five mL of LB (100 μg/ml amp). This five mL sample was incubated overnight at 37° C. while shaking at 235 RPM. A 50 mL LB (100 μg/ml amp) subculture was inoculated with the overnight culture. This subculture was grown at 37° C. with shaking (235 RPM) until reaching an $OD_{600}$ in a range of 0.5-0.8. Once at mid-log, the cell culture was induced with IPTG to a final concentration of 1.0 mM. The temperature was dropped to 20° C. and the cells were grown for 16 hours while shaking at 235 RPM. After the 16 hours, the bacterial cells were pelleted using centrifugation at 8,000 RPM for 15 minutes and stored at −20° C.

TABLE 3

Ec IspE (SEQ ID NOS 5-6, respectively) and Bt IspE (SEQ ID NOS 7-8, respectively) DNA and protein sequences.

| Ec IspE | Bt IspE |
|---|---|
| DNA Sequence | DNA Sequence |
| ATGGCGCATCATCATCATCATCATATGCGCACCCAGTGGCCGAGCCCGGC<br>GAAACTGAACCTGTTTCTGTATATTACCGGCCAGCGCGCGGATGGCTATC<br>ATACCCTGCAGACCCTGTTTCAGTTTCTGGATTATGGCGATACCATTAGCA<br>TTGAACTGCGCGATGATGGCGATATTCGCCTGCTGACCCCGGTGGAAGGC<br>GTGGAACATGAAGATAACCTGATTTGCGCGCGGCGCGCCTGCTGATGAA<br>AACCGCGGCGGATAGCGGCCGCCTGCCGACCGGCAGCGGCGCGAACATT<br>AGCATTGATAAACGCCTGCCGATGGGCGGCGGCCTGGGCGGCGGCAGCA<br>GCAACGCGGCGACCGTGCTGGTGGCGCTGAACCATCTGTGGCAGTGCGG<br>CCTGAGCATGGATGAACTGGCGGAAATGGGCCTGACCCTGGGCGCGGAT<br>GTGCCGGTGTTTGTGCGCGGCCATGCGGCGTTTGCGGAAGGCGTGGGCGA<br>AATTCTGACCCCGGTGGATCCGCCGGAAAAATGGTATCTGGTGGCGCATC<br>CGGGCGTGAGCATTCCGACCCCGGTGATTTTTAAAGATCCGGAACTGCCG<br>CGCAACACCCCGAAACGCAGCATTGAAACCCTGCTGAAATGCGAATTTA<br>GCAACGATTGCGAAGTGATTGCGCGCAAACGCTTTCGCGAAGTGGATGCG<br>GTGCTGAGCTGGCTGCTGGAATATGCGCCGAGCCGCCTGACCGGCACCG<br>GCGCGTGCGTGTTTGCGGAATTTGATACCGAAAGCGAAGCGCGCCAGGTG<br>CTGGAACAGGCGCCGGAATGGCTGAACGGCTTTGTGGCGAAAGGCGTGA<br>ACCTGAGCCCGCTGCATCGCGCGATGCTG | ATGGCTCATCACCATCACCATCATATGGGTACCCTGGAAGCTCAGACCCA<br>GGGTCCTGGTTCGATGACCGATACGACCCGCTCGCTGCGCGACTGCCTCG<br>CCCCGGCGAAACTGAACCTGTTCCTGCACATCACGGGCCGTCGTCCGGA<br>CGGCTATCACGAGCTGCAAAGCGTGTTCCAGCTGCTCGACTGGGGCGACC<br>GGCTGCACTTCACGCTGCGCGACGACGGCAAGGTGTCGCGCAAGACCGA<br>CGTGCCGGGCGTACCCGAGGAAACCGACCTCATCGTGCGCGCGGCGTCG<br>CTGCTGAAAGCGCACACGGGCACGGCGGCGGGCGTCGACATCGAGATCG<br>ACAAGCGACTGCCGATGGGCGCGGGCCTCGGCGGAGGCAGCTCGGATGC<br>GGCGACGACGTTGCTCGCGCTCAACCGCCTCTGGAAGCTCGACTTGCCGC<br>GCGCCACGCTGCAATCGCTCGCGGTGAAGCTCGGCGCCGACGTGCCGTT<br>CTTCGTCTTCGGAAAAAATGCGTTCGCAGAGGGTATCGGAGAAGCGCTGC<br>AAGCTGTAGAATTGCCGACTCGCTGGTTTCTGGTTGTGACACCGCGGGTTC<br>ACGTTCCGACCGCAGCGATTTTTTCCGAAAAATCGTTGACAAGAGATTCG<br>AAACCATCACAATTACGGACTTTCTTGCACAGCAAGACTGCAACACGGG<br>ATGGCCTGACAGTTTCGGTCGGAATGACATGCAGCCGGTTGTGACAAGCA<br>AGTACGCGGAAGTTGCAAAGGTGGTCGGATGGTTTTATAATCTGACCCCC<br>GCGCGGATGACCGGCTCCGGAGCTAGCGTGTTTGCAGCGTTCAAGAGCAA<br>GGCGGAGGCAGGAGCGGCGCAAGCCCAACTGCCGGCCGGCTGGGACAG<br>CGCAGTTGCCGAGAGCTTGGGTGAGACATCCACTCTTCGCTTTCGCGTCA |
| Protein Sequence | Protein Sequence |
| MAHHHHHHMRTQWPSPAKLNLFLYITGQRADGYHTLQTLFQFLDYGDTISIE<br>LRDDGDIRLLTPVEGVEHEDNLIVRAARLLMKTAADSGRLPTGSGANISID<br>KRLPMGGGLGGGSSNAATVLVALNHLWQCGLSMDELAEMGLILGADVPVFVR<br>GHAAFAEGVGEILIPVDPPEKWYLVAHPGVSIPISVIFKDPELPRNTPKRSI<br>ETLLKCEFSNDCEVIARKRFREVDAVLSWLLEYAPSRLTGTGACVFAEFDTE<br>SEARQVLEQAPEWLNGFVAKGVNLSPLHRAML | MAHHHHHHMGTLEAQTQGPGSMTDTTRSLRDCLAPKLNLFHITGRRPDG<br>YHELQSVFQLLDWGDRLHFTLRDDGKVSRKTDVPGVPEETDLIVRAASL<br>LKAHTGTAAGVDIEIDKRLPMGAGLGGGSSDAATTLLALNRLWKLDLPR<br>ATLQSLAVKLGADVPFFVFGKNAFAEGIGEALQAVELPTRWFLVVTPRV<br>HVPTAAIFSEKSLTRDSKPIITTDFLAQQDCNTGWPDSFGRNDMQPVVT<br>SKYAEVAKVVGWFYNLTPARMTGSGASVFAAFKSKAEAGAAQAQLPAGW<br>DSAVAESLGEHPLFAFAS |

Both *Escherichia coli* and *Burkholderia thailandensis* IspE were purified using a HisTrap HP nickel affinity IMAC column (GE Healthcare Life Sciences) with a BioLogic LP (Bio-Rad Life Sciences) fast protein liquid chromatography (FPLC) system with a 20-500 mM gradient elution using imidazole. Fractions associated with the UV absorbance peak in the chromatogram, verified with a NanoDrop 2000c spectrophotometer (Thermo Scientific), were combined and concentrated to 10 mL using a spin concentrator. The resulting concentrate was further purified using a size exclusion chromatography column (Superdex 75 HiLoad 26/60 GE Healthcare Life Sciences), and fractions related to the UV absorbance peak of IspD were collected, combined, and concentrated. The protein was aliquoted and stored at −80° C. prior to enzymatic assays.

Pyrazolopyrimidines were used in a Kinase-Glo® enzymatic assay against both *E. coli* and *B. thailandensis*. The Kinase-Glo® assay follows the consumption of the reactant ATP. The ATP in conjunction with oxygen and beetle luciferin are catalyzed by luciferase with the cofactor of magnesium to produce oxyluciferin, AMP, carbon dioxide, pyrophosphate, and creates a luminescence signal. This luminescence is directly related to the amount of ATP within the reaction, as the reaction progresses, the ATP is consumed and the amount of luminescence is decreased.

All Kinase-Glo® reactions were run using the following conditions (all conditions are described in final concentrations): 60 mM NaCl, 5 mM $MgCl_2$, 20 mM HEPES, 1 mM DTT, 5% DMSO (for compound suspension), 0.01% BSA, 200 μM CDP-ME, 40 μM ATP, and either Ec IspE or Bt IspE. All but the substrate CDP-ME were combined and incubated with the compounds for 10 minutes, before the addition of substrate and incubation (45 minutes, with shaking, room temperature). After incubation, the Kinase-Glo® reagent was added in equal final volume and allowed to develop for 10 minutes. Luminescence was recorded via a Synergy 2 plate reader. Dose response curves for compounds 18, 22, 23, and 29 are shown in FIGS. 5-8, respectively.

It is to be understood that use of the indefinite articles "a" and "an" in reference to an element (e.g., "a compound," "a bacterial infection," etc.) does not exclude the presence, in some embodiments, of a plurality of such elements.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present disclosure. Thus, whereas the dependent claims appended below may depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A compound of formula (I)

(I)

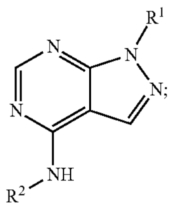

or a pharmaceutically acceptable salt thereof;

wherein $R^1$ is methyl; and wherein $R^2$ has a formula (VIII)

(VIII)

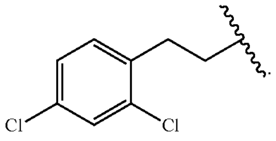

2. A compound of formula (I)

(I)

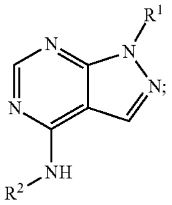

or a pharmaceutically acceptable salt thereof;

wherein $R^1$ comprises an alkyl group;

wherein $R^2$ comprises an optionally substituted group of formula (III)

(III)

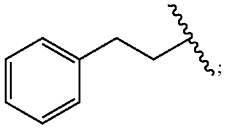

and wherein the group of formula (III) comprises a lipophilic electron withdrawing group at each of its 2-position and 4-position.

* * * * *